(12) United States Patent
Lopez et al.

(10) Patent No.: US 10,207,299 B2
(45) Date of Patent: Feb. 19, 2019

(54) SYSTEMS AND METHODS FOR ACTIVE BIOFOULING CONTROL

(71) Applicant: DUKE UNIVERSITY, Durham, NC (US)

(72) Inventors: Gabriel P. Lopez, Durham, NC (US); Vrad W. Levering, Durham, NC (US); Xuanhe Zhao, Durham, NC (US); Phanindhar Shivapooja, Durham, NC (US); Qiming Wang, Durham, NC (US)

(73) Assignee: Duke University, Durham, NC (US)

( * ) Notice: Subject to any disclaimer, the term of this patent is extended or adjusted under 35 U.S.C. 154(b) by 1297 days.

(21) Appl. No.: 14/347,672

(22) PCT Filed: Sep. 28, 2012

(86) PCT No.: PCT/US2012/058000
§ 371 (c)(1),
(2) Date: Mar. 27, 2014

(87) PCT Pub. No.: WO2013/049626
PCT Pub. Date: Apr. 4, 2013

(65) Prior Publication Data
US 2014/0230854 A1 Aug. 21, 2014

Related U.S. Application Data

(60) Provisional application No. 61/540,051, filed on Sep. 28, 2011.

(51) Int. Cl.
*A61M 5/32* (2006.01)
*B08B 7/02* (2006.01)
(Continued)

(52) U.S. Cl.
CPC ............ *B08B 7/02* (2013.01); *A01N 25/34* (2013.01); *A61M 25/0017* (2013.01);
(Continued)

(58) Field of Classification Search
CPC .......... A61M 5/32; A61M 27/00; A61F 5/44; B65D 83/10; B65D 81/02
See application file for complete search history.

(56) References Cited

U.S. PATENT DOCUMENTS 4,469,483 A * 9/1984 Becker .............. A61M 25/0108
128/DIG. 21
4,843,854 A 7/1989 Ackerly
(Continued)

FOREIGN PATENT DOCUMENTS

EP 0874783 B1 5/2003
WO PCT/US2009/049154 A1 11/2010
WO 2013049626 A1 4/2013

OTHER PUBLICATIONS

Extended European Search Report dated Aug. 5, 2015 for European Patent Application 12836413.0.
(Continued)

*Primary Examiner* — Tatyana Zalukaeva
*Assistant Examiner* — Ilya Treyger
(74) *Attorney, Agent, or Firm* — Olive Law Group, PLLC

(57) ABSTRACT

Disclosed herein are devices and methods for active biofouling control. According to an aspect, a device comprising a surface for contacting a biological material. The device also comprises a mechanism comprising a structure configured to change the surface between a first shape and a second shape. The change from the first shape to the second shape deforms the surface beyond a critical strain for debonding of a fouling agent from the surface when the fouling agent has bonded to the surface in the first shape.

16 Claims, 26 Drawing Sheets

(51) Int. Cl.
*A01N 25/34* (2006.01)
*A61M 25/00* (2006.01)
*A61M 27/00* (2006.01)
*A61F 5/44* (2006.01)
*B65D 83/10* (2006.01)
*B65D 81/02* (2006.01)
*B08B 17/06* (2006.01)

(52) U.S. Cl.
CPC . *A61M 25/0023* (2013.01); *A61M 2025/0019* (2013.01); *A61M 2025/0024* (2013.01); *A61M 2025/0025* (2013.01); *B08B 17/06* (2013.01)

(56) References Cited

U.S. PATENT DOCUMENTS

| | | |
|---|---|---|
| 5,551,460 A | 9/1996 | Runion |
| 5,879,623 A | 3/1999 | Glover et al. |
| 2005/0256410 A1 | 11/2005 | Rabiner et al. |
| 2005/0267421 A1 | 12/2005 | Wing |
| 2011/0004197 A1 | 1/2011 | Sansoucy |

OTHER PUBLICATIONS

Supplementary Examination Written Opinion for Singapore Application No. 11201401087W dated May 5, 2016.

International Search Report and Written Opinion dated Feb. 20, 2013, for corresponding PCT patent application No. PCT/US2012/058000, and references cited therein.

Supplementary Examination Report from the Intellectual Property Office of Singapore for Patent Application Serial No. 11201401087W, dated Sep. 13, 2016.

Communication under Rule 71(3) EPC issued in counterpart EP Application No. 12836413.0 dated Jun. 26, 2018. (Sixty-three (63) pages).

\* cited by examiner

| Shear Modulus (MPa) / Electric Field (10MV/m) | 0.060 | 0.155 | 0.365 |
|---|---|---|---|
| 2.3 | 12 ± 2.3 | 10 ± 2.6 | 11 ± 2 |
| 4.2 | 87 ± 7.1 | 16 ± 1.7 | 16 ± 5.5 |
| 7.0 | 88 ± 6 | 95 ± 2.7 | 11 ± 1.3 |
| 11.7 | 90 ± 3.6 | 96 ± 2.8 | 97 ± 1.6 |

Table 1.

FIG. 35

SYSTEMS AND METHODS FOR ACTIVE BIOFOULING CONTROL

CROSS REFERENCE TO RELATED APPLICATION

This application is a 35 USC 371 application of International PCT Patent Application No. PCT/US12/58000, filed Sep. 28, 2012, which claims priority to and the benefit of U.S. Provisional Patent Application No. 61/540,051, filed Sep. 28, 2011 and titled SYSTEMS AND METHODS FOR ACTIVE BIOFOULING CONTROL, the contents of which are hereby incorporated herein by reference in their entireties.

FEDERALLY SPONSORED RESEARCH OR DEVELOPMENT

The invention was made with government support under Grant No.'s N00014-08-0741 and N00014-10-1-0907 each awarded by the U.S. Office of Naval Research, and under Grant No. DMR-1121107 awarded by the National Science Foundation. The United States government has certain rights in the invention.

TECHNICAL FIELD

The presently disclosed subject matter relates to devices and methods for active biofouling control.

BACKGROUND

Biofouling is a problem that plagues a host of industrial operations, military operations and medical treatments worldwide and that represents costs in excess of 1 to 100 billion dollars annually. It remains a significant fundamental problem that can significantly hinder humankind's ability to manipulate biological systems. Accordingly, it is desired to provide devices and techniques for control of biofouling in a variety of applications.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are devices and methods for active biofouling control. According to an aspect, a device comprising a surface for contacting a biological material. The device also comprises a mechanism comprising a structure configured to change the surface between a first shape and a second shape. The change from the first shape to the second shape deforms the surface beyond a critical strain for debonding of a fouling agent from the surface when the fouling agent has bonded to the surface in the first shape.

According to another aspect, a system comprises an electrode and a layer attached to the electrode and defining a surface for contacting a biological material. The system also comprises a voltage source configured to apply voltage between the electrode and the biological material such that the surface is changed between a first shape and a second shape. The change from the first shape to the second shape deforms the surface beyond a critical strain for debonding of a fouling agent from the surface when the fouling agent has bonded to the surface in the first shape.

According to another aspect, a device is provided for detaching cellular components from a surface. The device comprises a surface for contacting a cellular component. Further the device comprises a mechanism configured to change the surface between a first shape in which a cellular component has become attached and a second shape. The change from the first shape to the second shape deforms the surface beyond a critical strain for detaching of the cellular component from the surface.

According to another aspect, a device comprises a sensor configured to measure a physical condition in a biological material and to generate a signal based on the measurement. The sensor comprises a surface to be exposed to the biological material. Further, the device comprises a covering that at least partially covers the surface of the sensor and that defines another surface for contacting the biological material. The device also comprises a mechanism configured to change the surface of a covering between a first shape and a second shape. The change from the first shape to the second shape deforms the surface of the covering beyond a critical strain for debonding of a fouling agent from at least a portion of the surface of the covering when the fouling agent has bonded to the surface of the sensor and the surface of the covering in the first shape such that at least a portion of the surface of the sensor is exposed to the biological material.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed.

FIG. 3E is a graph showing the quantification of cell densities on each polymer film.

FIG. 11(a) illustrates diagrams of the debonding mechanism at two different stages of operation in accordance with embodiments of the present disclosure. FIG. 11(b) depicts an image showing the detachment of barnacles from a stretched elastomer film. FIG. 11(c) depicts an image showing the shear stress needed in this example to detach barnacles from the elastomer film decreases with the applied strain on the film. The elastomers are periodically stretched uniaxially to a prescribed strain for 30 cycles within 3 minutes. FIG. 11(d) depicts a graph illustrating the adhesion strengths for barnacle-SYLGARD 184 and barnacle-ECOFLEX systems.

FIG. 35 illustrates Table 1 depicting Electric Field Shear Modulus (Mpa) calculation results.

DETAILED DESCRIPTION

Figure 1:
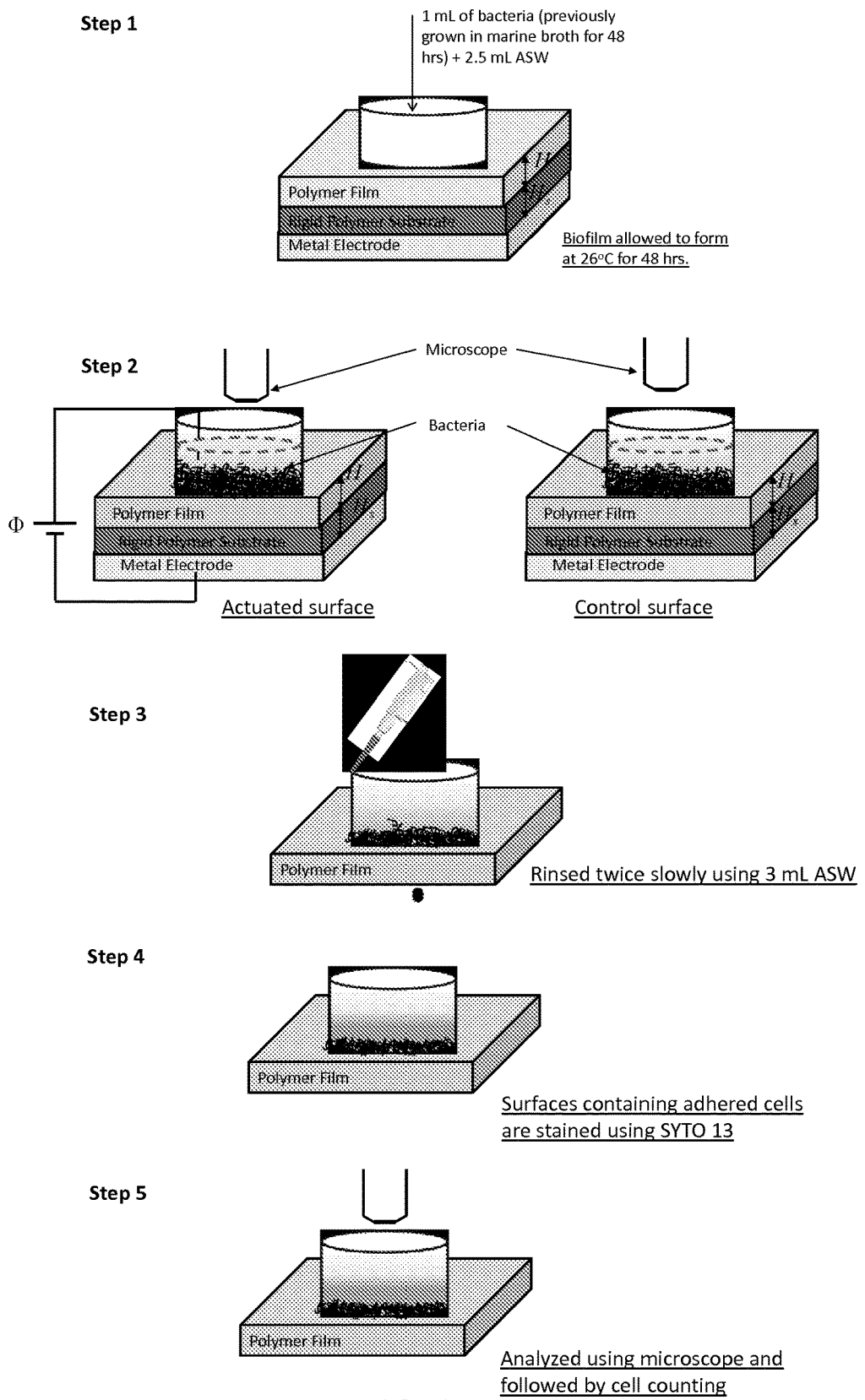
FIG. 1 shows a schematic of the procedure used in the experiments provided herein.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Unless otherwise defined, all technical terms used herein have the same meaning as commonly understood by one of ordinary skill in the art to which this disclosure belongs.

The articles "a" and "an" are used herein to refer to one or to more than one (i.e., at least one) of the grammatical objects of the article. By way of example, "an element" means at least one element and can include more than one element.

In describing various embodiments of the present disclosure illustrated in the drawings, specific terminology is employed for the sake of clarity.

However, the presently disclosed subject matter is not intended to be limited to the specific terminology so selected, and it is to be understood that each specific element includes all technical equivalents that operate in a similar manner to accomplish a similar purpose.

The dynamic elastomeric films disclosed herein have many applications, including equipment or vessels upon which it is desired to inhibit the accumulation of biofouling. Examples would include any situation where the material would be in a wetted environment, such as a ship or boat hull, a heat exchanger, or medical devices such as catheters, stents, IV tubing, respiratory tubing and the like. One finding by the inventors is that deformation of the elastomeric film that can serve to detach the fouling agent. This deformation may occur through the application of voltages, or by mechanical means, such as stretching, bending, twisting and the like. Hence, the actuation of the polymer film may be used either to prevent the settlement and attachment of fouling biological or chemical species, or as a "duty-cycle" to remove fouling material that has accumulated during periods between actuation. Simultaneous application of fluid shear may be employed to remove detached or de-adhered fouling species from the vicinity of the elastomer surface.

The presently disclosed subject matter provides techniques and devices for actively and effectively detaching micro- and macro-fouling organisms through dynamic change of surface area and topology of elastomers in response to external stimuli. These dynamic surfaces can be fabricated from materials used in marine coatings and medical devices and can be actuated by electrical and pneumatic stimulation. New antifouling management strategies based on active surface deformation can also be used in combination with other existing and emerging management approaches for biofouling.

In accordance with embodiments of the present disclosure, a structure is provided that can prevent the adherence of, or allows for the removal of, a fouling agent when exposed to an aqueous environment. As used herein, the term "fouling agent" refers to the undesirable accumulation of microorganisms, plants, algae, and/or animals on a wetted surface. Also within the scope of the presently disclosed subject matter, the term "fouling agent" may refer to the accumulation of a desired cell type, prokaryotic or eukaryotic, that one would want to recover from a surface after it has been accumulated. Examples of such fouling agents include, but are not limited to, bacterial accumulations or other such films desired for biochemical analysis, fungal or other such accumulations used in biotechnology, or accumulations of mammalian cells used in regenerative medicine or other medical procedures or research. The structure comprises, consists of, or consists essentially of a soft polymer layer and an actuation means, wherein the actuation means is capable of deforming the soft polymer layer beyond the critical strain for debonding ($\varepsilon_c$) of the fouling agent.

The applications of the presently disclosed subject matter include such applications as, for example, debonding of a number of biological films and adsorbates including those formed by: (i) marine and industrial biofouling; (ii) culture of mammalian cells; and (iii) formation of infectious biofilms on medical implants. An example of the latter is the problematic infectious biofilms that can form on medical implants such as indwelling catheters, which are often constructed of elastomers. According to the devices, methods, and systems provided herein, problematic biofilms can be released from such catheters by subjecting their polymer surfaces to cyclic changes in surface area. The deformation of the polymer surfaces can effectively detach microbial biofilms and macro-fouling organisms.

As used herein, the term "critical strain" refers to any change in any area of the surface of the soft polymer or other material in accordance with the present disclosure. For example, in some embodiments where electrical actuation is applied, the surface area may change (i.e., the surface is strained/puckered), however the entire width or length of the soft polymer film does not. In other instances, the entire width and/or length may be changed, such as when the soft polymer film is stretched, pulled, twisted, and the like.

As used herein, the action terms "change a shape" or "changing a shape" of a surface can refer to either changing an area of the surface, any distorting of the surface, or any other type of changing of a surface from one shape to another shape.

In another example, the presently disclosed subject matter provides devices, methods, and systems that include a mechanism that includes a structure that is configured to change the surface of a device between a first shape and a second shape such that the change from the first shape to the second shape deforms the surface beyond a critical strain for debonding of a fouling agent from the surface when the fouling agent has bonded to the surface in the first shape. The use of the term "shape" is meant in its broadest sense. For example, a change in shape as it is used herein deforms the surface beyond a critical strain for debonding of a fouling agent. A change in shape can include a change in a total surface area but such a change in total surface area is not required.

In one example, a soft polymer layer may be exposed to the aqueous environment upon which the fouling agent may attach, or may be prevented from attaching. The soft polymer layer may be an inert, non-toxic and non-flammable substance. Suitable materials include, but are not limited to, polydimethyl siloxane (PDMS) or other silicone rubber, acrylic elastomer, a polyurethane, a fluoroelastomer, and the like.

The thickness of the soft polymer layer should be such that application of the actuation means will be able to cause deformation. Suitable thicknesses may be between 10 nm to 1 mm, or between 1 µm to about 500 µm. Similarly, the soft polymer layer may have a Young's modulus of between about 0.5 KPa to about 2.0 MPa, or between 1.0 KPa to about 1.0 MPa.

In certain embodiments, the soft polymer layer may be coated, such as spin coated, or coated on the rigid polymer film. In other embodiments, the outer surface of the soft polymer layer (i.e., the side facing the wetted environment) may be textured. As used herein, the term "texture" refers to any permutation of the elastomer surface that makes it not smooth, such as ridges, creases, holes, etc. In certain embodiments, the soft polymer layer comprises a corrugated surface.

In yet other embodiments, the surface of the soft polymer layer may also be modified by chemical means to further improve greater fouling resistance or fouling release. Such modifications include, but are not limited to, coating the polymer surface with hydrated polymers such as poly(ethyleneglycol)-derivatives, polyzwitterions and polymer brushes or coatings with other types of polymers, and the like.

The structure further comprises an actuation means. As used herein, the term "actuation means" refers to any means that is able to put the soft polymer layer into action or motion. In some embodiments, the actuation means may be one that applies a mechanical force to the soft polymer layer, which may be beyond the critical strain for debonding of the fouling agent. As detailed in the Examples section, one finding of the presently disclosed subject matter is how the application of a mechanical force, such as stretching, of the soft polymer layer had a surprising and dramatic effect on the ability of fouling agents to remain adhered to the surface. Suitable mechanical forces include, but are not limited to, stretching, squeezing, twisting, shaking and the like.

In other embodiments, the actuation means comprises an electrical actuation means. Suitable electrical actuation means includes any device capable of generating a voltage of at least 20 kV. In those embodiments wherein electric actuation means is used, the structure further comprises a rigid polymer layer having a top side and a bottom side, where the soft polymer layer is attached to the top side of the rigid polymer layer. Further, the outer surface of the soft polymer layer is exposed to an electrolyte solution (e.g., water) and the bottom side of the rigid polymer layer comprises an electrically conductive material that is capable of allowing a voltage to pass through the polymer layers with respect to the electrolyte. Suitable materials include, but are not limited to, thin layers of conductive metals, such as gold, silver, aluminum, tin, copper and the like, a conductive tape such as carbon tape, a conductive oxide, such as indium tin oxide, a semiconductor, and the like.

The rigid polymer layer may comprise any material that is nonreactive. Examples of suitable material include, but are not limited to, polytetrafluoroethylene (PTFE; TEFLON), poly(4,4'-oxydiphenylene-pyromellitimide (KAPTON), polyethylene and the like. Also suitable for the rigid polymer layer are nonpolymeric insulating films, such as ceramics.

The thickness of the rigid polymer layer should be such that application of a voltage will be able to deform the soft polymer layer. Suitable thicknesses may be between 10 nm to about 1 µm, or between 1 µm to about 500 µm. Similarly, the rigid polymer layer may have a Young's modulus of between about 0.5 GPa to about 200 GPa, or between 1 GPa to about 100 GPa.

In use, a voltage is applied between the electrolyte solution in contact with the outer surface of the soft polymer layer and the conductive electrode coated on the rigid polymer layer. This ωολταγε causes the soft polymer layer to deform beyond the critical strain for debonding ($\varepsilon_c$) of the fouling agent. In certain embodiments, the applied voltage can be between about 0 V and about 20 kV, or between about 100 V and about 8 kV, or between about 3 kV and about 6 kV. The appropriate voltage may depend on several factors, such as the properties of the polymer films (e.g., Young's modulus, thickness, material, etc.) and the like, and can be readily determined by one skilled in the art. In other embodiments, voltage comprises an oscillating voltage. The length of time that the electric current is generated may be between 15, 14, 13, 12, 11, 10, 9, 8, 7, 6, 5, 4, 3, 2, or 1 minutes. In some embodiments, the electric current is generated for at least 5 minutes.

Another aspect of the presently disclosed subject matter provides a method of removing a fouling agent from, or preventing a fouling agent from adhering to, a surface exposed to an aqueous solution comprising deforming the surface beyond the critical strain for bonding or debonding ($\varepsilon_c$) of the fouling agent. In certain embodiments, the surface comprises a soft polymer layer and a mechanical actuation means. In such embodiments, a mechanical force, such as stretching, twisting, squeezing, shaking, etc., is sufficiently applied to deform the surface of the soft polymer film beyond the critical strain for bonding of the fouling agent, thereby causing the fouling agent to become unattached from the soft polymer layer, or be unable to attach to, the soft polymer layer.

In other embodiments. the surface comprises a rigid polymer layer having a top side and bottom side, the bottom side being coated with a conductive electrode coating, and a soft polymer layer attached to the top side of the rigid polymer layer, with the soft polymer layer being exposed to an electrolyte solution (e.g., water). In such embodiments, a voltage is applied in a sufficient amount to cause the deformation of the soft polymer layer beyond the critical strain for debonding ($\varepsilon_c$) of the fouling agent, thereby either causing the attached fouling agents to become unbounded from the polymer surface, or preventing the fouling agent(s) from bonding to the soft polymer surface.

Figure 10:
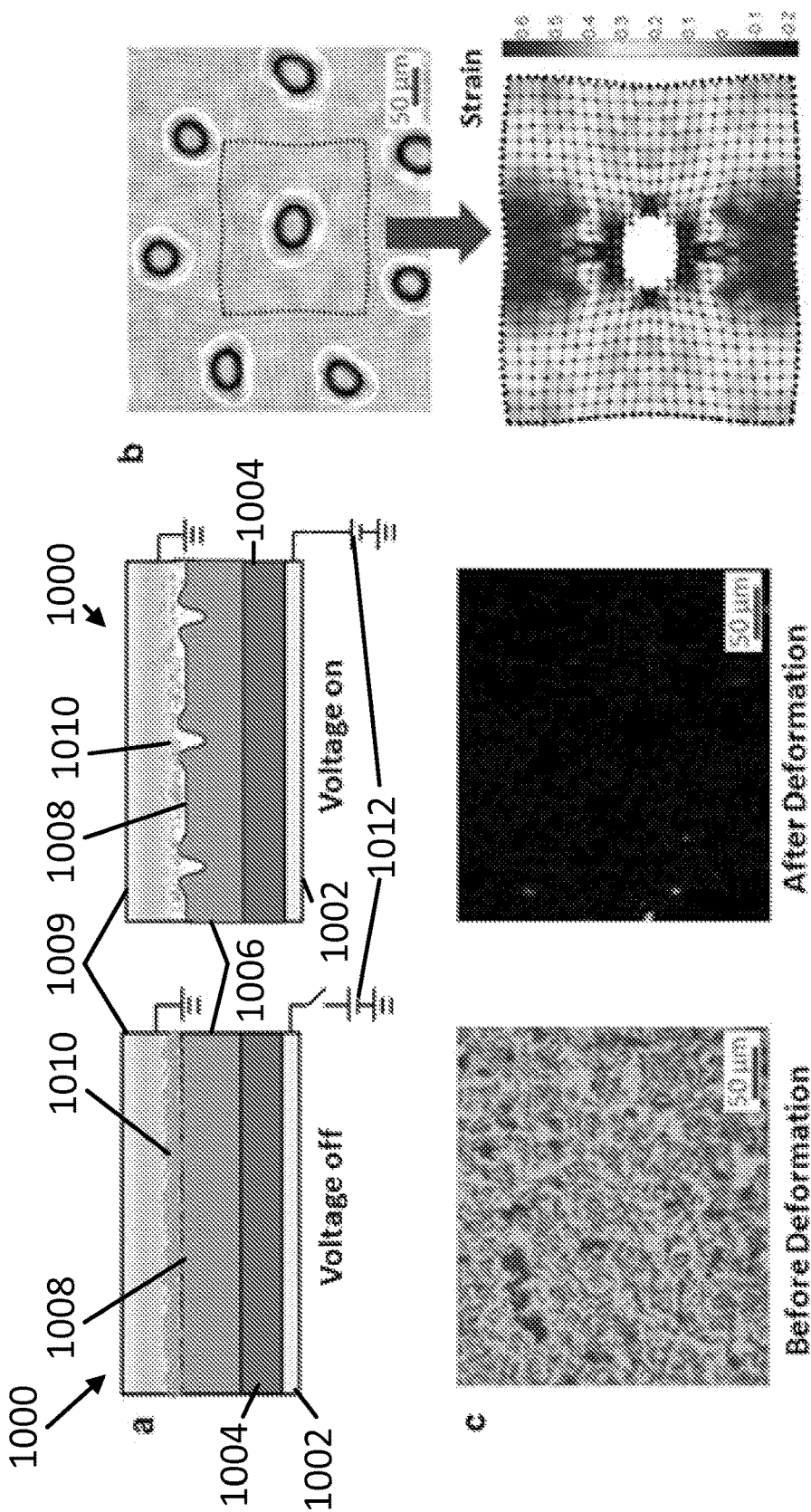
FIG. 10 illustrates debonding of biofilms from stretched elastomer films. (a) Schematic illustration of the debonding mechanism. (b) Percentage of detachment of C. marina biofilm as a function of the applied strain. (c) Percentage of detachment of E. coli biofilm as a function of the applied strain. The elastomers are periodically stretched uniaxially to a prescribed strain for 30 cycles within 3 minutes.

FIG. 10 illustrates debonding of barnacles from stretched elastomer films. Particularly, FIG. 10(a) illustrates diagrams of the debonding mechanism at two different stages of operation in accordance with embodiments of the present disclosure. FIG. 10(b) depicts an image showing the detachment of barnacles from a stretched elastomer film. FIG. 10(c) depicts an image showing the shear stress needed in this example to detach barnacles from the elastomer film decreases with the applied strain on the film. The elastomers are periodically stretched uniaxially to a prescribed strain for 30 cycles within 3 minutes.

Referring particularly to FIG. 10(a), the diagrams depict a system 1000 in different stages: "voltage off" and "voltage on". The system 1000, in this example, includes multiple layers 1002, 1004, and 1006. Layer 1002 may be a conductive layer or any other suitable conductive component. As an example, the layer 1002 may include, but is not limited to, a metal, conductive tape, conductive oxide, semiconductor, or combinations thereof. The layer 1006 may be disposed on or otherwise attached to the layer 1002. A surface 1008 of the layer 1006 may be textured and may contact a biological material 1009, such as material within a marine environment (e.g., sea water). The layer 1006 may be a polymer coating. The coating may be applied by a suitable spincoating technique. Further, for example, the layer 1006 may include, for example, but not limited to, polytetrafluoroethylene, poly(4,4'-oxydiphenylene-pyromellitimide, polyethylene, ceramics, or the like. Further, for example, the layer 1006 may include polydimethyl siloxane, silicone rubber, acrylic elastomer, polyurethane, fluoroelastomer, or the like. The layer 1006 may have a thickness of between about 10 μm and 1 mm, or more particularly a thickness of between about 1 μm and 500 μm. Further, the layer 1006 may have a Young's modulus of between about 0.5 KPa and about 2 MPa, or more particularly a Young's modulus of between about 1 KPa and about 1 MPa.

The system 1000 may include a voltage source 1012 configured to apply voltage between the conductive layer 1002 and the biological material 1009 such that the surface 1008 of the layer 1006 is changed between a first shape shown in the diagram labeled "Voltage off" and a second shape shown in the diagram labeled "Voltage on". For example, the voltage applied by the voltage source 1012 is off initially when a fouling agent 1010 has bonded to the surface 1008. The voltage may be applied such that the fouling agent 1010 debonded as shown in the diagram labeled "Voltage on". In an example, the applied voltage may be an oscillating voltage, which may be between about 0.1 Hz and about 100 Hz, or about 0.5 Hz and about 10 Hz. Further, the applied voltage may be between about 0 kV and about 20 kV, between about 100 V and about 8 kV, or between about 3 kV and about 6 kV. The voltage may be applied for 5 or more minutes in one example. A suitable controller may be used to control the voltage source 1012 to change the applied voltage for changing the surface between the first shape and the second shape.

The layer 1004 may be any suitable layer positioned between the layers 1002 and 1006. For example, layer 1004 may be a KAPTON layer. The (e.g., compression and stretching) layer may act as a buffer substrate that prevents the electric field in the deformed PDMS film to become excessively high. KAPTON has a modulus of 3 orders of magnitude greater than the PDMS. So, any rigid polymer of comparable modulus as KAPTON can be used in place of layer 1004 if needed. The layer may prevent the top polymer film from deforming excessively and from electrical breakdown. The layer may be constituted of a rigid insulating material which can be rigid polymers such as KAPTON, TEFLON, polyethelene, an insulating glass, ceramic, or the like.

Figure 11:
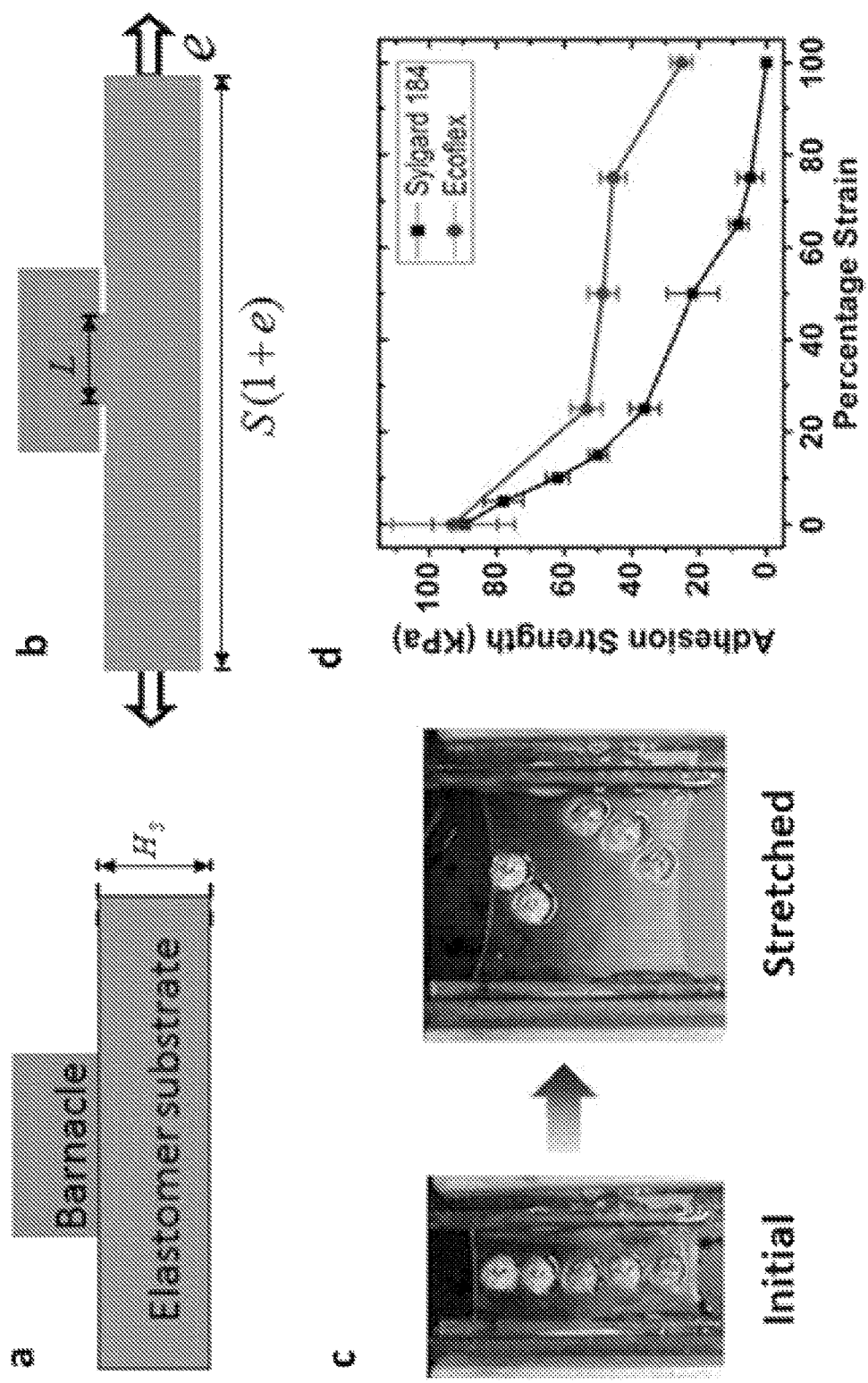
FIG. 11 illustrates debonding of barnacles from stretched elastomer films. Particularly.

FIG. 11 illustrates debonding of barnacles from stretched elastomer films. Particularly, FIG. 11(*a*) illustrates diagrams of the debonding mechanism at two different stages of operation in accordance with embodiments of the present disclosure. FIG. 11(*b*) depicts an image showing the detachment of barnacles from a stretched elastomer film. FIG. 11(*c*) depicts an image showing the shear stress needed in this example to detach barnacles from the elastomer film decreases with the applied strain on the film. The elastomers are periodically stretched uniaxially to a prescribed strain for 30 cycles within 3 minutes.

Referring particularly to FIG. 11(*a*), the diagrams depict a system 1100 in different stages: "voltage off" and "voltage on". The system 1100, in this example, includes multiple layers 1102, 1104, and 1106. Layer 1102 may be a conductive layer or any other suitable conductive component. As an example, the layer 1102 may include, but is not limited to, a metal, conductive tape, conductive oxide, semiconductor, or combinations thereof. The layer 1106 may be disposed on or otherwise attached to the layer 1102. A surface 1108 of the layer 1106 may be textured and may contact a biological material 1109, such as material within a marine environment (e.g., sea water). The layer 1106 may be a polymer coating. The coating may be applied by a suitable spincoating technique. Further, for example, the layer 1106 may include, for example, but not limited to, polytetrafluoroethylene, poly(4,4'-oxydiphenylene-pyromellitimide, polyethylene, ceramics, or the like. Further, for example, the layer 1106 may include polydimethyl siloxane, silicone rubber, acrylic elastomer, polyurethane, fluoroelastomer, or the like. The layer 1106 may have a thickness of between about 10 μm and 1 mm, or more particularly a thickness of between about 1 μm and 500 μm. Further, the layer 1106 may have a Young's modulus of between about 0.5 KPa and about 2 MPa, or more particularly a Young's modulus of between about 1 KPa and about 1 MPa.

The biological material 1109 may comprise an electrolyte solution. In this example, the system 1100 can be manufactured on a boat hull, marine sensor, or the like. As shown in the diagram labeled "Voltage off," the system 1100 has been within the environment for a sufficient time such that a fouling agent 1110 has bonded to the surface 1108.

Figure 17:
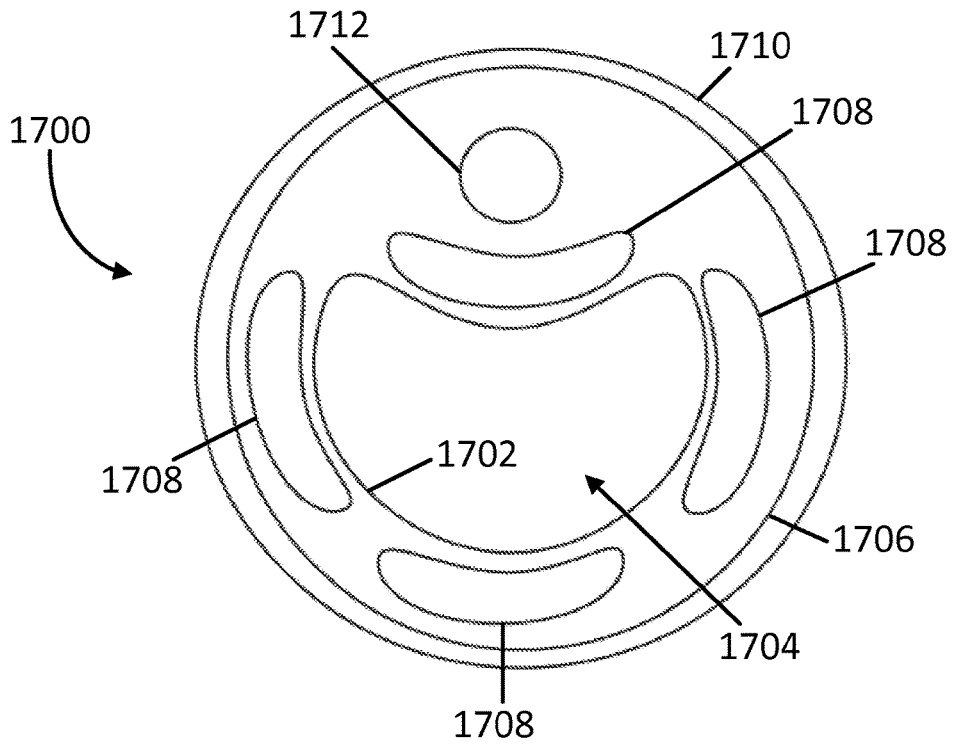
FIG. 17 is a cross-section view of a device having a structure for debonding of a fouling agent from a surface of the device having come in contact with a biological material in accordance with embodiments of the present disclosure.
Figure 18:
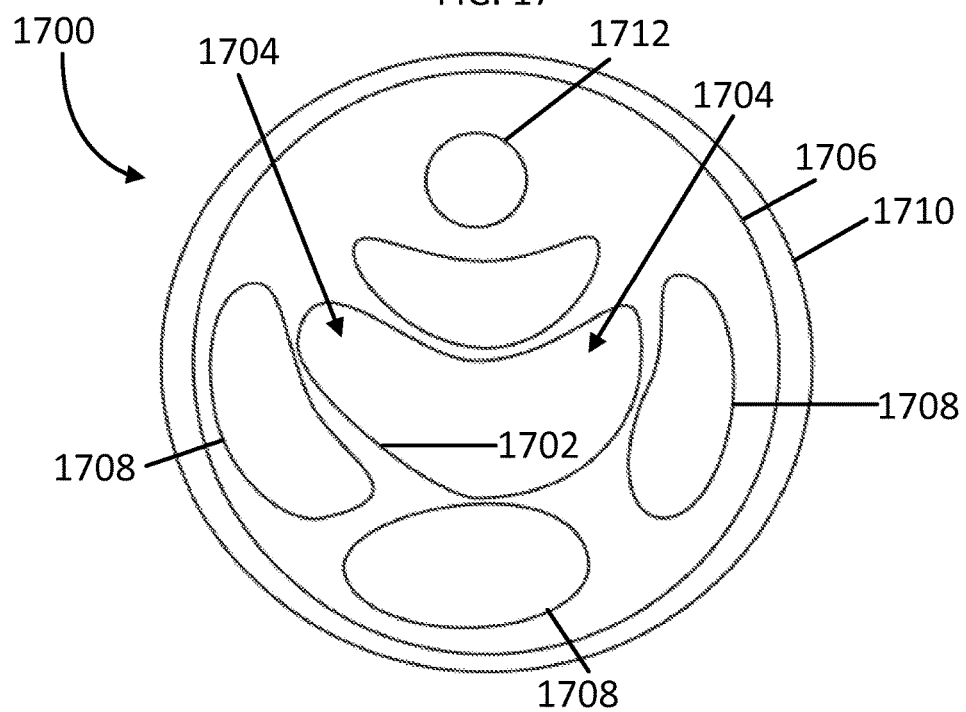
FIG. 18 is a cross-section view of the device shown in FIG. 17.

Referring particularly to FIG. 17, FIG. 17 is a cross-sectional top view of a device 1700 having a surface 1702 for contacting a biological material 1704, and a mechanism including a structure 1706 configured to change the surface 1702 between a first shape and a second shape in accordance with embodiments of the present disclosure. The change of the surface 1702 of the device 1700 from the first shape to the second shape deforms the surface 1702 beyond a critical strain for debonding of a fouling agent from the surface 1702 when the fouling agent has bonded to the surface 1702 in the first shape. FIG. 18 is the same cross-sectional top view of the device 1700 showing the change in the surface 1702 between the first and second shapes. A fouling agent that has become bonded to the surface 1702 of the device 1700 in contact with a biological material 1704 can be debonded by changing the surface 1702 between the first and second shapes. The fouling agent can be any undesirable accvμulation of microorganisms, plants, algae, and/or animals and more specifically, for example, bacteria, a biofilm, a bacterial biofilm, crystalline biofilmsor, thrombus, and fibrous capsules.

In one embodiment, the surface 1702 of the device 1700 can define a lumen for contacting the biological material 1704. For example, the surface 1702 of the device 1700 can define a lumen 1704 of a catheter. The structure 1706 of the device 1700 can be configured to apply a mechanical force to the surface 1702 for changing the surface 1702 between the first shape and the second shape. The surface 1702 can be defined by a material and the mechanism for causing the surface to change between the first shape and the second shape can be to apply pneumatic pressure to the material. The surface 1702 can be defined by a material comprising a polymer. The material can comprise one or more of polydimethyl siloxane, silicone rubber, acrylic elastomer, polyurethane, or fluoroelastomer.

As illustrated in FIGS. 17 and 18, the surface 1702 of the device 1700 can define a lumen for contacting the biological material 1704 and the structure configured to deform the surface 1702 beyond a critical strain for debonding of a fouling agent can define at least one cavity 1708 that substantially surrounds the lumen 1704 and is configured to be inflated and deflated such that the cavity 1708 impinges on the lumen 1704 when inflated to change the surface 1702 from the first shape to the second shape and when deflated to change the surface 1702 back to the first shape. In another example in accordance with embodiments of the present disclosure, the surface 1702 of the device 1700 can define a lumen 1704, and the mechanism can include a structure 1706 defining at least one cavity 1708 that substantially surrounds the lumen 1704 and impinges on the lumen 1704 in the first shape and is configured to be deflated and inflated such that the cavity ceases to impinge on the lumen when deflated to change the surface from the first shape to the second shape.

The device 1700 can include a high durometer sheath 1710 substantially surrounding the one or more cavities 1708. The surface 1702 of the device 1700 can define a lumen 1704 of a catheter. The surface 1702 of the device 1700 can define a lumen 1704 of a catheter and the catheter can be a urinary catheter.

Figure 19:
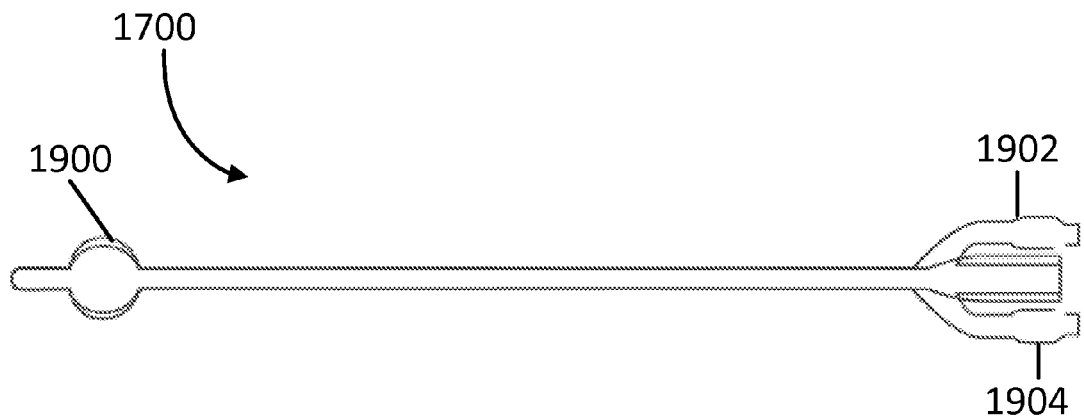
FIG. 19 is a side view of the device shown in FIG. 17.

The device 1700 can include an aperture 1712 for a balloon structure 1900 configured to be inflated on an internal-positioned end and comprising an external-positioned inflation port 1902 configured for inflation of the internal-positioned end, such that inflation of the balloon structure 1900 after insertion holds the catheter in place. FIG. 19 is a side view of a device 1700 in accordance with embodiments of the present disclosure that illustrates the inflatable balloon structure 1900. FIG. 19 also illustrates that the at least one cavity 1708 of the device 1700 can be fluidly connected to a pump port 1904 configured to inflate and deflate the at least one cavity 1708. The pump port 1904 can be configured to inflate and deflate the at least one cavity 1708 via user application of a syringe. The pump port 1904 can be configured to inflate and deflate the at least one cavity 1708 via application of pneumatic pressure. The pump port 1904 can be configured to inflate and deflate the at least one cavity 1708 via application of a fluid.

Figure 20:
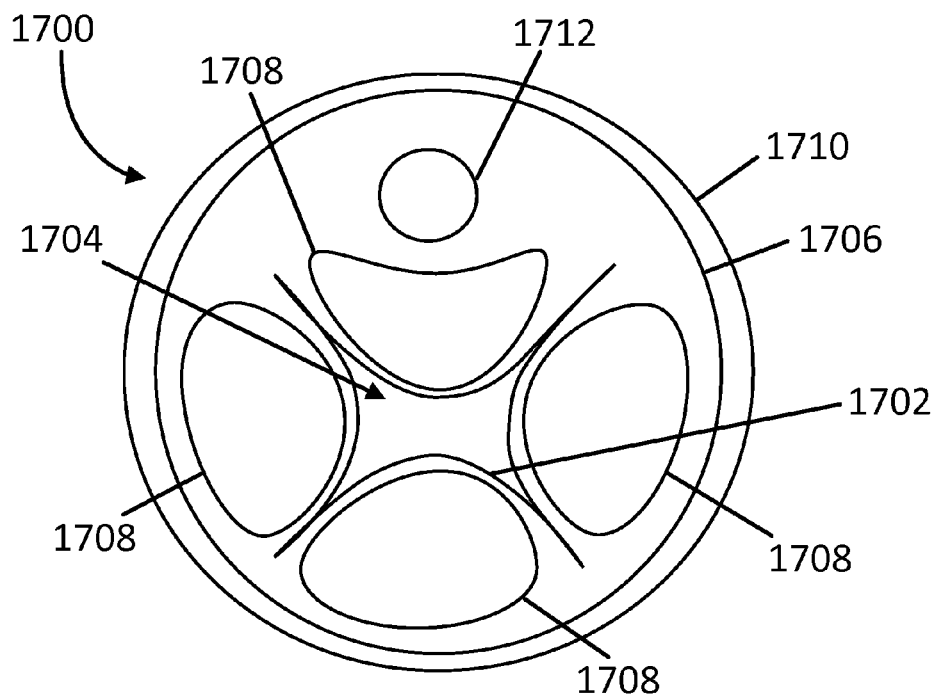
FIG. 20 is a cross-section view of the device shown in FIG. 17.
Figure 21:
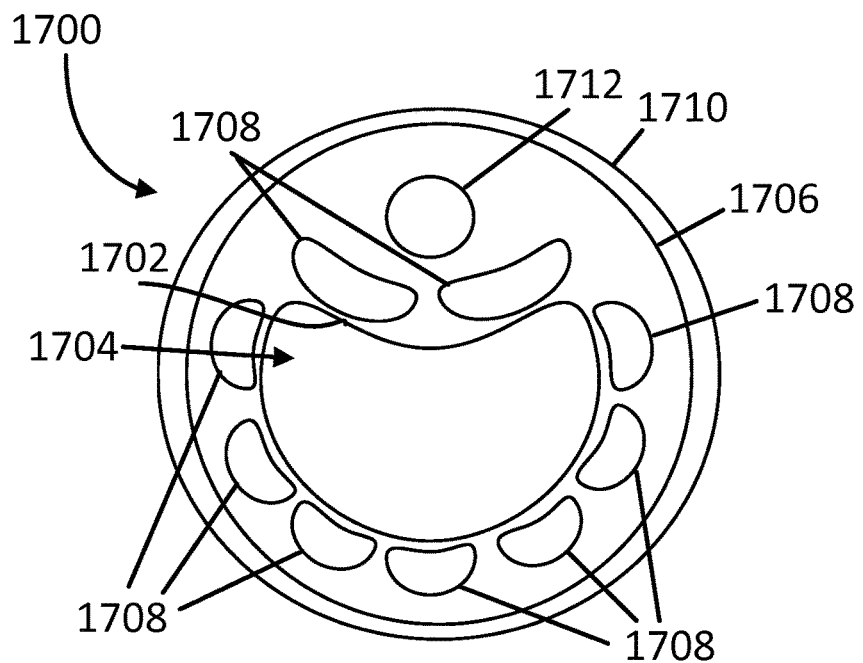
FIG. 21 is a cross-section view of a device having a structure for debonding of a fouling agent from a surface of the device having come in contact with a biological material in accordance with embodiments of the present disclosure. The device shown has nine cavities.
Figure 22:
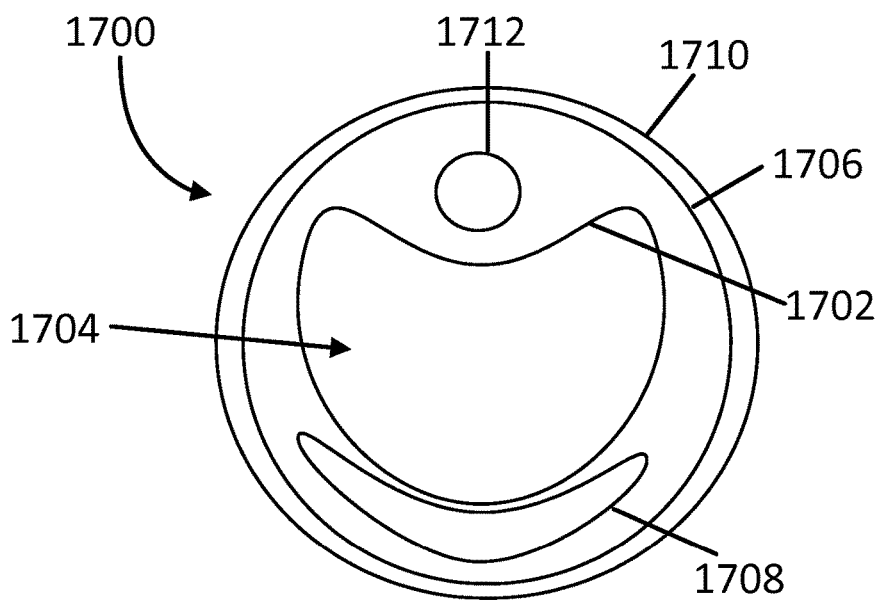
FIG. 22 is a cross-section view of a device having a structure for debonding of a fouling agent from a surface of the device having come in contact with a biological material in accordance with embodiments of the present disclosure. The device shown has a single cavity.

FIGS. 20-22 are cross-sectional top views of the device 1700 having a surface 1702 for contacting a biological material 1704, and a mechanism including a structure 1706 configured to change the surface 1702 between a first shape and a second shape in accordance with embodiments of the present disclosure. The devices 1700 illustrated in FIGS. 20-22 include structures 1706 defining a range of numbers of cavities 1708. For example, the device 1700 shown in FIG. 20 has four cavities 1708, the device 1700 shown in FIG. 21 has nine cavities 1708, and the device 1700 shown in FIG. 22 has a single cavity 1708. Referring to FIG. 20, the lumen 1704 when inflated causes portions of the surface 1702 to contact each other such that fouling agent can be scrubbed away from the surface or otherwise dislodged.

Figure 23:
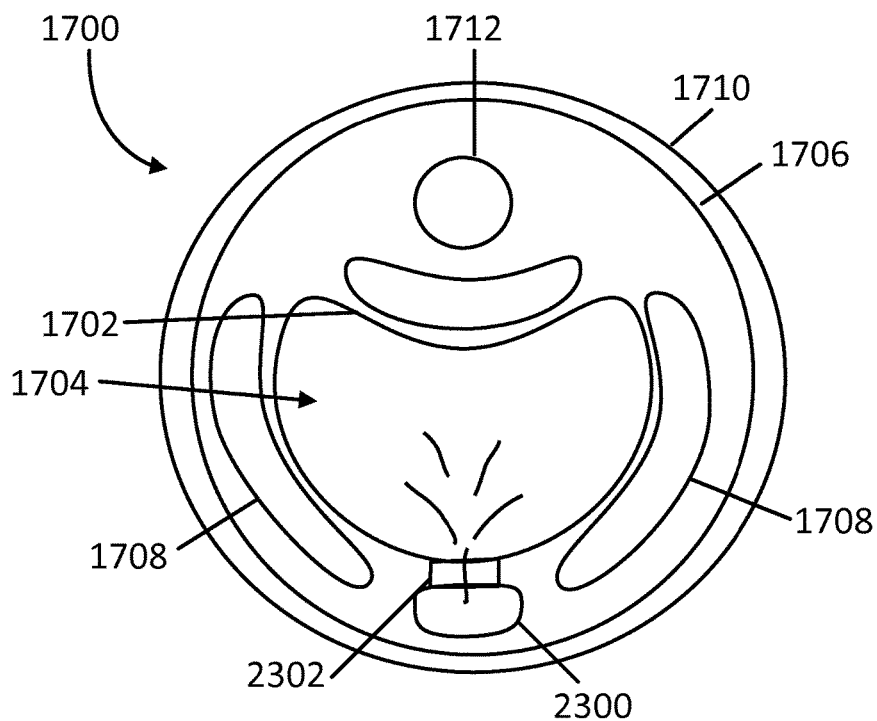
FIG. 23 is a cross-section view of a device having a structure for debonding of a fouling agent from a surface of the device having come in contact with a biological material in accordance with embodiments of the present disclosure. The device has a second lumen for flushing of the first lumen.
Figure 24:
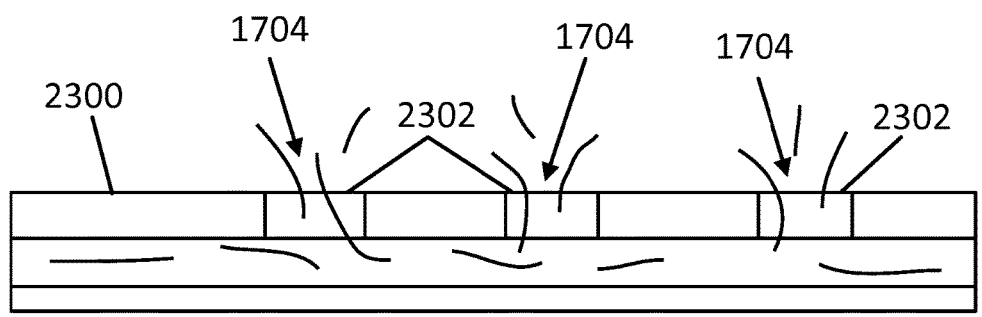
FIG. 24 is a cross-section view through the fluid connection between the first and second lumen along a length of the device shown in FIG. 23.

FIG. 23 illustrates a cross-sectional top view of the device 1700 that has a surface 1702 that defines a first lumen 1704 for contacting a biological material and a second lumen 2300 fluidly connected 2302 to the first lumen 1704. The second lumen is fluidly connected to the first lumen at one or more positions along a length of the first lumen 2300 and is configured to direct a flushing fluid into the first lumen. FIG. 24 is a cross-sectional view illustrating the fluid connection 2302 between the first 1704 and second 2300 lumen along a length of the device 1700. The second lumen 2300 can be used to inject flushing fluid including, for example, pharmaceuticals or biofilm loosening agents. The flushing fluid can be used prior to inflation and deflation of the cavities 1708 or alternatively during inflation and deflation to increase debonding and detachment of the fouling agent. The device 1700 can include one or more injection ports for the flushing fluid.

Figure 25:
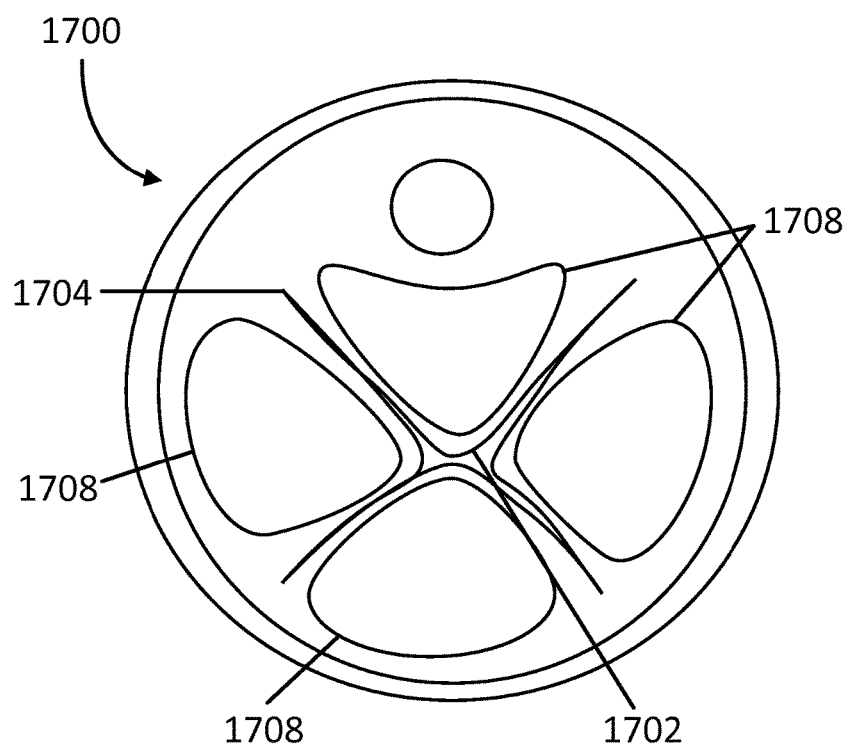
FIG. 25 is a cross-section view of the device shown in FIG. 17 and illustrates how the sides of the lumen can come into contact with each other when the four cavities are inflated in accordance with embodiments of the present disclosure.
Figure 26:
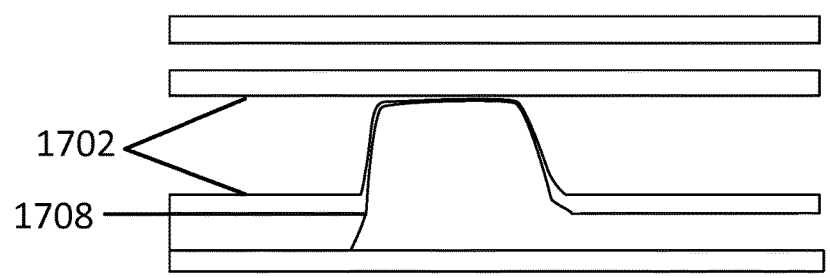
FIG. 26 is a side view of the device shown in FIG. 25 with just one cavity inflated to effectively seal off the cavity.

FIG. 25 is a cross-sectional top view of the device 1700 shown in FIG. 17 and illustrates an embodiment in which different portions of the surface 1702 of the lumen 1704 have come into contact with each other when the cavities 1708 are inflated to change to the second shape. FIG. 26 is a cross-sectional side view of the device 1700 of FIG. 25 in which one of the cavities 1708 is inflated and depicts the contacting of the different portions of the surface 1702 of the lumen 1704. The surface of the device 1700 illustrated in FIGS. 25 and 26 can define a lumen 1704 and the lumen can be a lumen of a urinary catheter. One reason that urinary catheters become infected is that the catheters drain at a slow rate, and therefore do not receive the flushing associated with urination that forcefully expels bacteria. Having the sides of the surface of the lumen of a urinary catheter device illustrated, for example, in FIGS. 25 and 26 contact each other would result in sealing of the urine pathway and would mimic bladder control cycles (e.g., bladder builds up a quantity of urine before releasing the seal to allow urine to flow). The side view shown in FIG. 26 with just one cavity 1708 inflated can effectively seal off the drainage of urine from the lumen 1704. Such a sealable lumen 1704 can allow for a more normal lifestyle and bladder cycle, and possibly elimination of bladder collection bags.

In one embodiment, the presently disclosed subject matter provides a method for debonding a fouling agent from a surface of a device, the method comprising changing a surface of a device between a first shape in which a fouling agent has become bonded through contact with a biological material and a second shape, such that the change from the first shape to the second shape deforms the surface beyond a critical strain for debonding of the fouling agent from the surface of the device. The surface of the device can define a lumen such as, for example, the device shown in FIGS. 17-26. The surface of the device can define a lumen of a catheter such as, for example, the device shown in FIGS. 17-26. The surface can be defined by a material comprising a polymer. The surface can be defined by a material comprising one of polydimethyl siloxane, silicone rubber, acrylic elastomer, polyurethane, or fluoroelastomer.

In one embodiment, the method for debonding a fouling agent from the surface of the device includes changing the surface between the first shape and the second shape by applying a mechanical force to the surface. The surface can be defined by a material, and applying the mechanical force can include applying pneumatic pressure to the material for causing the surface to change between the first shape and the second shape. The surface of the device can define a lumen such as, for example, the device shown in FIGS. 17-26. The surface of the device can define a lumen of a catheter such as, for example, the device shown in FIGS. 17-26. The surface can be defined by a material comprising a polymer. The surface can be defined by a material comprising one of polydimethyl siloxane, silicone rubber, acrylic elastomer, polyurethane, or fluoroelastomer.

In one embodiment of the method, the surface 1702 of the device 1700 shown in FIGS. 17-26 can define a lumen 1704, and the method for debonding a fouling agent from the surface 1702 can further include providing a structure 1706 defining at least one cavity 1708 that substantially surrounds the lumen 1704, and changing the surface 1706 can include inflating the at least one cavity 1708 such that the at least one inflated cavity 1708 impinges on the lumen 1704 and changes the surface 1702 from the first shape to the second shape. The at least one cavity 1708 can be fluidly connected to a pump port 1904 configured to inflate the at least one cavity 1708. Inflating the at least one cavity 1708 can include applying pneumatic pressure. Inflating the at least one cavity 1708 can include application of a liquid. The device 1700 can further include a high durometer sheath 1710 substantially surrounding the at least one cavity 1708. The lumen 1704 can be a lumen of a catheter. The lumen 1704 can be a lumen of a urinary catheter. In one embodiment, the method for debonding a fouling agent from the surface 1702 of the catheter can include providing a balloon structure 1900 configured to be inflated on an internal end through an inflation port 1902 such that inflation of the balloon structure 1900 after insertion holds the catheter in place.

In one embodiment of the method, the surface 1702 of the device 1700 defines a lumen 1704 and the method for debonding a fouling agent from the surface 1702 of the lumen 1704 can include providing a structure 1706 defining at least one cavity 1708 that substantially surrounds the lumen 1704 and impinges on the lumen, and changing the surface 1702 by deflating and inflating the at least one cavity 1708 such that the deflated cavity 1708 ceases to impinge on the lumen 1704 and changes the surface 1702 from the first shape to the second shape.

The various number and orientation of the cavities shown 1708 in the devices 1700 illustrated in FIGS. 17-26 allow for alteration of the mechanical stress (e.g., compression and stretching) applied to the surface having the bonded fouling agent to effect debonding and detachment of the fouling agent. In addition, the number and orientation of the cavities can allow for extreme inflation to achieve large surface area distortion of the lumen 1704 without luminal rubbing or can allow for degrees of luminal rubbing to further increase the mechanical stress to effect fouling agent debonding and detachment. In one or more embodiments, the different cavities may be individually inflated and deflated for varying the mechanical stress on the surface. In this manner, the shape of the surface can be varied to a greater degree to effect debonding of the fouling agent.

In one embodiment of the method, the surface 1702 of the device 1700 illustrated in FIGS. 23 and 24 can define a first lumen 1704, and the device 1700 can further include a second lumen 2300 fluidly connected 2302 to the first lumen 1704 at one or more positions along a length of the first lumen 1704 configured to direct a flushing fluid into the first lumen 1704. The second lumen 2300 can be used to inject flushing fluid including, for example, pharmaceuticals or biofilm loosening agents. The flushing fluid can be used prior to inflation and deflation of the cavities 1708 or alternatively during inflation and deflation to increase debonding and detachment of the fouling agent. The device 1700 can include one or more injection ports for the flushing fluid.

In accordance with embodiments of the present disclosure, a device for detaching cellular components is provided. The device includes a surface for contacting a cellular component. For example, the surface may define a tissue scaffold, a cell culture scaffold, various processing equipment, or the like for holding a cellular component. Example cellular components include, but are not limited to, a cell culture, a tissue culture, a biofilm, and the like. The device may include a mechanism configured to change the surface between a first shape in which a cellular component has become attached and a second shape, such that the change from the first shape to the second shape deforms the surface beyond a critical strain for detaching of the cellular component from the surface. In an example, the mechanism may be in accordance with any of the embodiments disclosed herein. As an example, the mechanism may be configured to apply a mechanical force to the surface for changing the surface between the first shape and the second shape. In another example, the mechanism is configured to apply pneumatic pressure to a material that defines the surface for causing the surface to change between the first shape and the second shape. In another example, the mechanism may include a structure defining at least one cavity positioned in proximity to the surface and configured to be inflated such that the cavity exerts a force on the surface to change the surface from the first shape to the second shape.

Figure 27:
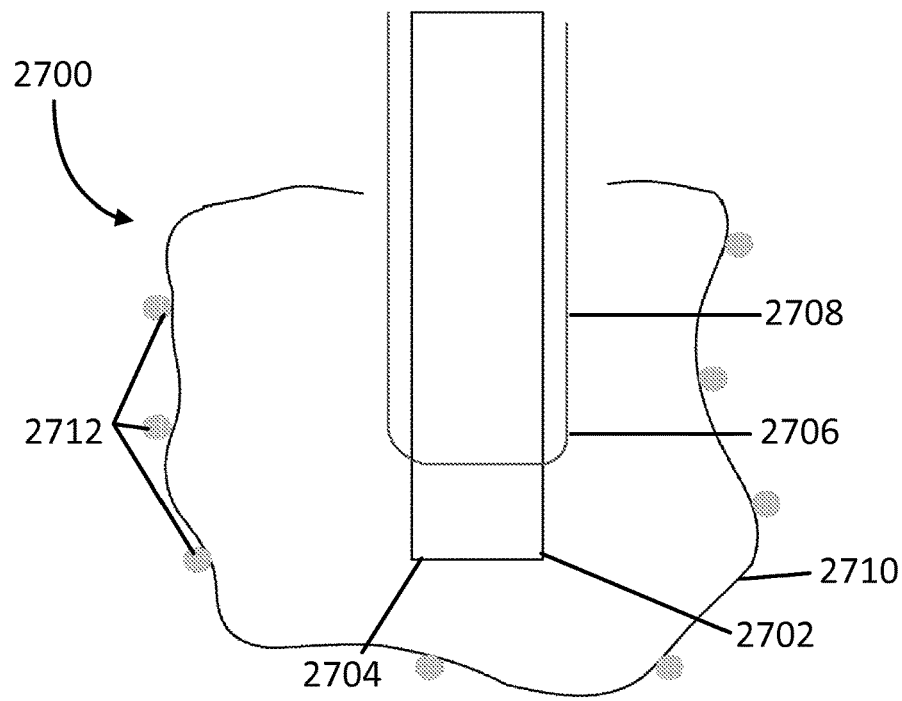
FIG. 27 illustrates a cross-sectional side view of a device for generating a signal to indicate a physical condition in a biological material and for debonding a fouling agent from a surface of a sensor of the system. The cross-section view shows a first shape of the surface of the covering on the device.

In accordance with embodiments of the present disclosure, devices and methods are provided that may be used in medical applications. The use of the present subject matter in medical applications can be particularly beneficial in the case of indwelling sensors such as glucose sensors. Such sensors can face long term (e.g., greater than 3 days) performance problems because fouling agents such as biofilms, thrombus, and fibrous capsules can form around the sensor and prevent penetration of an analyte (e.g., glucose) to the sensor. As an example device in accordance with embodiments of the present disclosure, FIG. 27 illustrates a cross-section side view of a device 2700 for generating a signal to indicate a physical condition in a biological material and for debonding a fouling agent from a surface of a sensor of the system. Referring to FIG. 27, the device 2700 includes a sensor 2702 configured to measure a physical condition in a biological material and to generate a signal based on the measurement. Further, the sensor 2702 may include one or more outer surfaces 2704 that can be exposed to a biological material. For example, the sensor 2702 may be an indwelling sensor such as, but not limited to, a glucose sensor. Other example include an oxygen sensor, a pH sensor, an arterial blood gases sensor, a temperature sensor, a carbon dioxide sensor, a toxic agents sensor, or any other sensors that may be immersed in bioactive environments.

Figure 28:
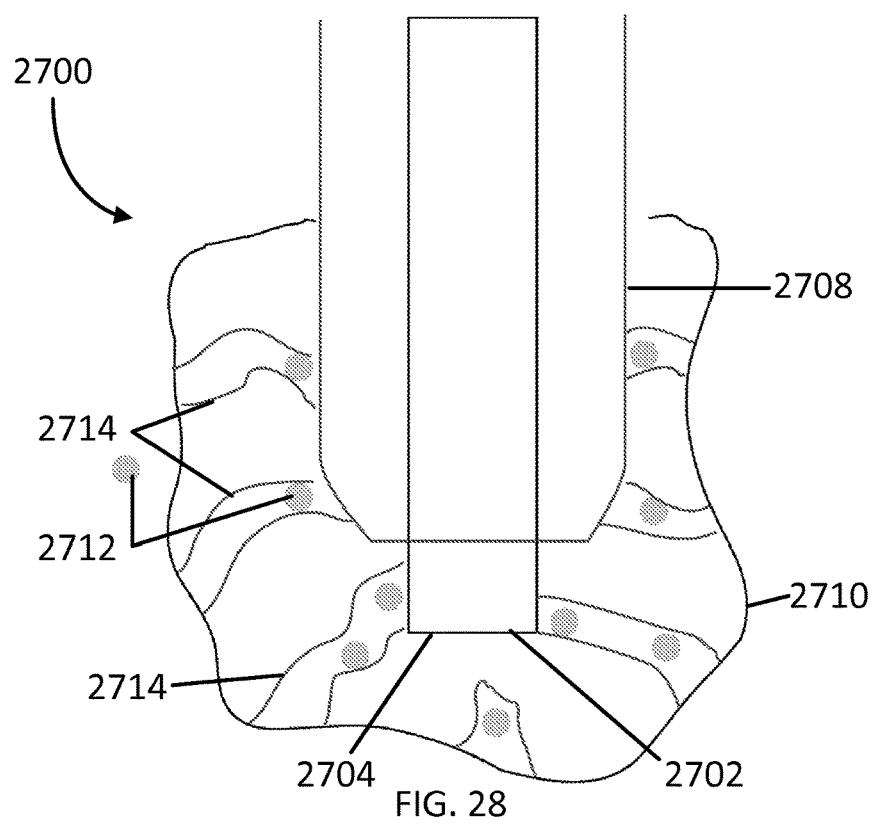
FIG. 28 illustrates a cross-sectional side view of the device shown in FIG. 27 and shows how the change from the first shape to the second shape of the surface of the covering has caused cracks allowing for access of an analyte to the device for measurement by the sensor.

The device 2702 may also include a covering 2706 that at least partially covers the surface 2704 of the sensor 2702. As shown in the figure, the covering 2706 does not cover a portion of the surface 2704 at a tip of the sensor such that the tip may be exposed to the biological material. The covering 2706 may cover the other portion of the sensor 2702 such that that portion is not exposed to the biological material. A mechanism may be suitable connected to the covering 2706 for causing a surface 2708 of the covering 2706 to change between a first shape shown in FIG. 27 and a second shape shown in FIG. 28. The change from the first shape to the second shape deforms the surface 2708 of the covering 2706 beyond a critical strain for debonding of a fouling agent 2710 from at least a portion of the surface 2708 of the covering 2706 when the fouling agent 2710 has bonded to the surface 2704 of the sensor 2702 and the surface 2708 of the covering 2706 in the first shape such that at least a portion of the surface 2704 of the sensor 2702 is exposed to the biological material.

In this example, the sensor 2704 is a glucose sensor configured to measure analytes 2712. As shown in FIG. 27, the fouling agent 2710 attaches to the sensor 2702 and the covering 2706. When the covering moves to the second shape shown in FIG. 28, cracks 2714 may form in the fouling agent 2710 such that the analytes 2712 may move to contact the surface 2704 of the sensor 2702 such that a measurement may be made. Alternatively, the fouling agent 2710 may be cleared substantially or entirely when the covering moves to the second shape.

In accordance with embodiments of the present disclosure, the mechanism for changing the shape of the surface 2708 of the covering 2706 may include one or more inflatable components that each defines a cavity disposed within the covering. For example, the inflatable components may be disposed within the covering 2706 and either partially or substantially surrounding the sensor 2702. The mechanism may also include a pump configured for fluid connection to the inflatable cavities and configured to inflate and deflate the cavities to change the surface 2708 of the covering 2706 between the first shape and the second shape. The pump may be, for example, a syringe suitable for inflating cavities as will be appreciated by those of skill in the art. The device 2700 may be suitably used to measure the physical condition and to generate the signal based on the measurement.

Figure 29:
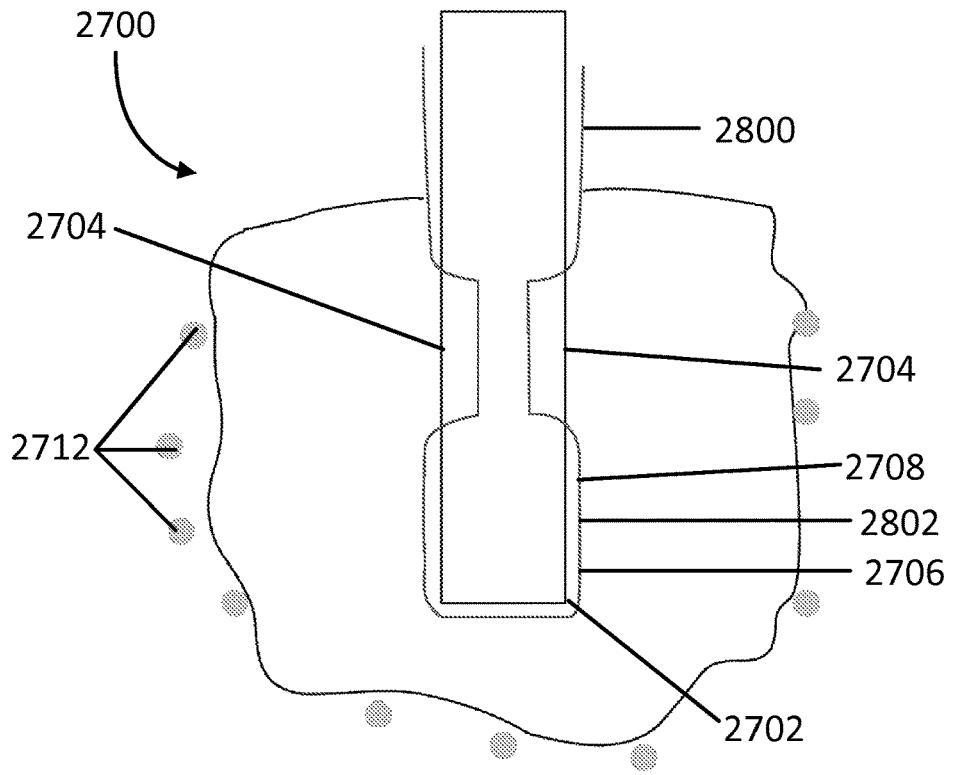
FIG. 29 illustrates a cross-sectional side view of another example device for generating a signal to indicate a physical condition in a biological material and for debonding a fouling agent from a surface of a sensor of the system in accordance with embodiments of the present disclosure.
Figure 30:
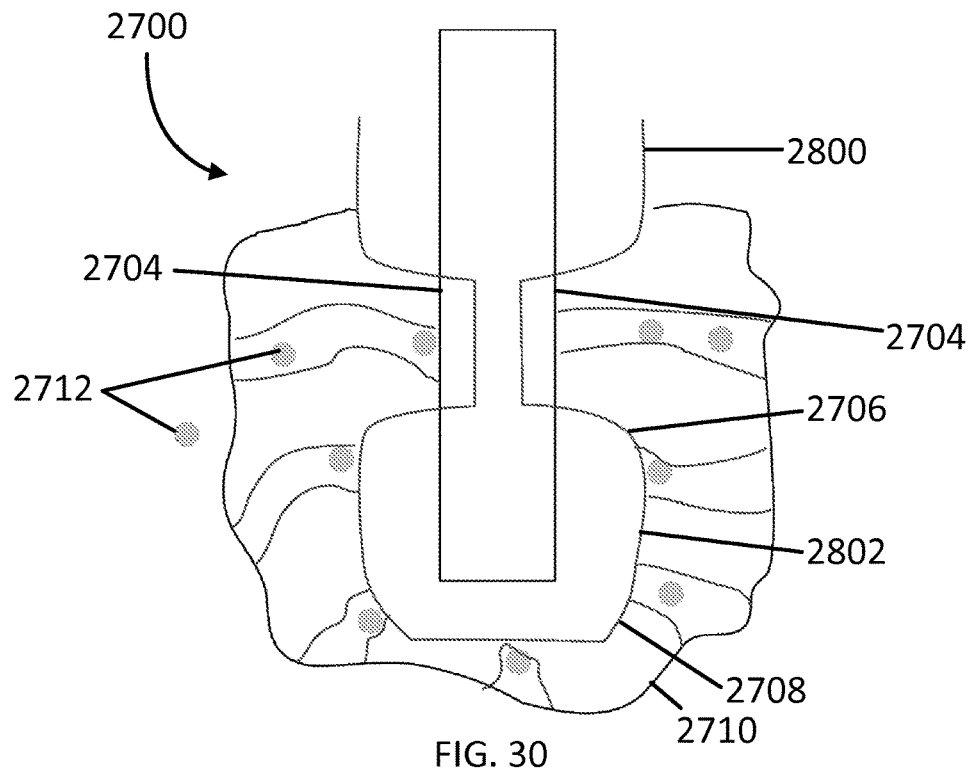
FIG. 30 illustrates cross-sectional side view of the device shown in FIG. 29 and shows how the change from the first shape to the second shape of the surface of the covering has caused cracks allowing for access of an analyte to the device for measurement by the sensor.

FIGS. 29 and 30 illustrate cross-section side views of another example device 2700 for generating a signal to indicate a physical condition in a biological material and for debonding a fouling agent from a surface of a sensor of the system in accordance with embodiments of the present disclosure. Referring to FIG. 29, the device 2700 is similar to the device shown in FIGS. 27 and 28 except that an exposed portion of the surface 2704 of the sensor 2702 is positioned between portions 2800 and 2802 of the covering 2706. One or more inflatable components may be disposed within the different portions 2800 and 2802. The analytes 2712 may pass through cracks 2714 to contact the sensor 2702 for measurement by the sensor 2702.

Figure 31:
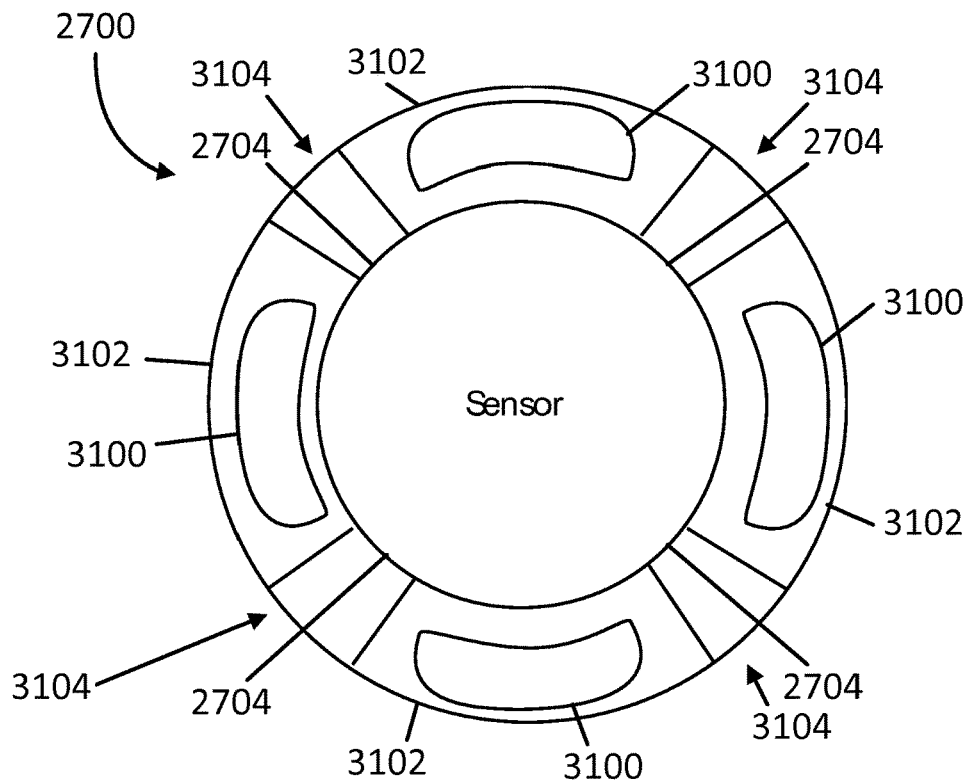
FIG. 31 illustrates a cross-sectional top view of an example device in accordance with embodiments of the present disclosure which includes multiple cavities formed by corresponding inflatable components.
Figure 32:
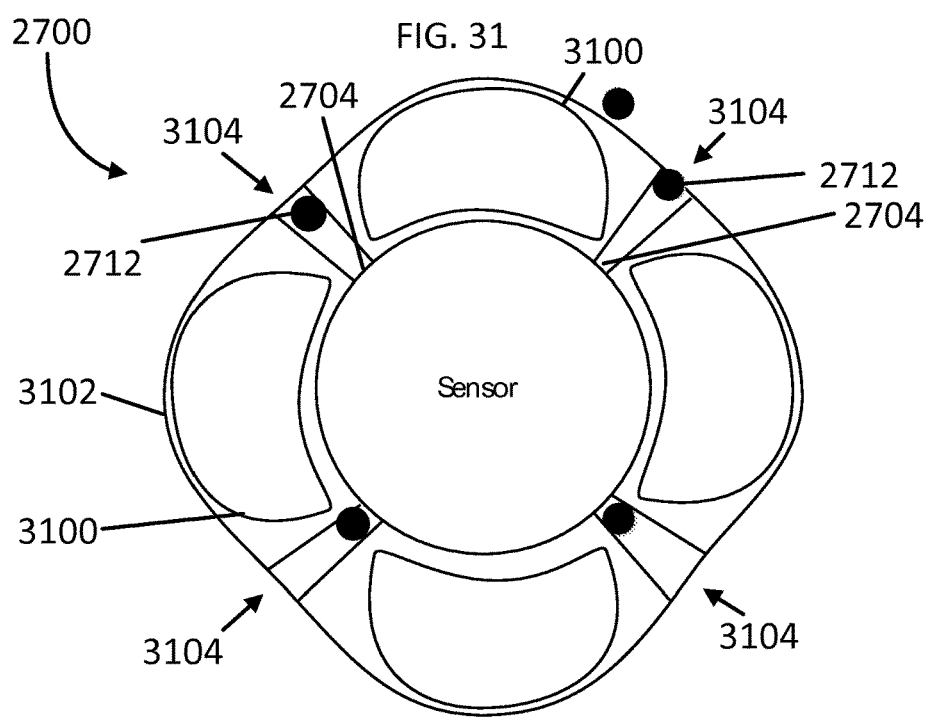
FIG. 32 illustrates a cross-sectional top view of the example device shown in FIG. 31 in a scenario in which the cavities are inflated.

FIG. 31 illustrates a cross-sectional top view of an example device 2700 in accordance with embodiments of the present disclosure. Referring to FIG. 31, the device 2700 includes multiple cavities 3100 formed by corresponding inflatable components 3102. A pump may suitably inflate the cavities 3100 for changing the surface 2708 to another position for debonding a fouling agent. The covering may include multiple pathways, generally designated 3104, that each lead to an exposed surface 2704 of the sensor. FIG. 32 illustrates a cross-sectional top view of the example device 2700 shown in FIG. 31 in a scenario in which the cavities 3100 are inflated. The pump may also extract air from the cavities 3100 for deflating the cavities 3100 such that the surface of the covering returns to the position shown in FIG. 31. FIG. 32 also shows the analytes 2712, some of which are positioned within the pathways 3104.

Figure 33:
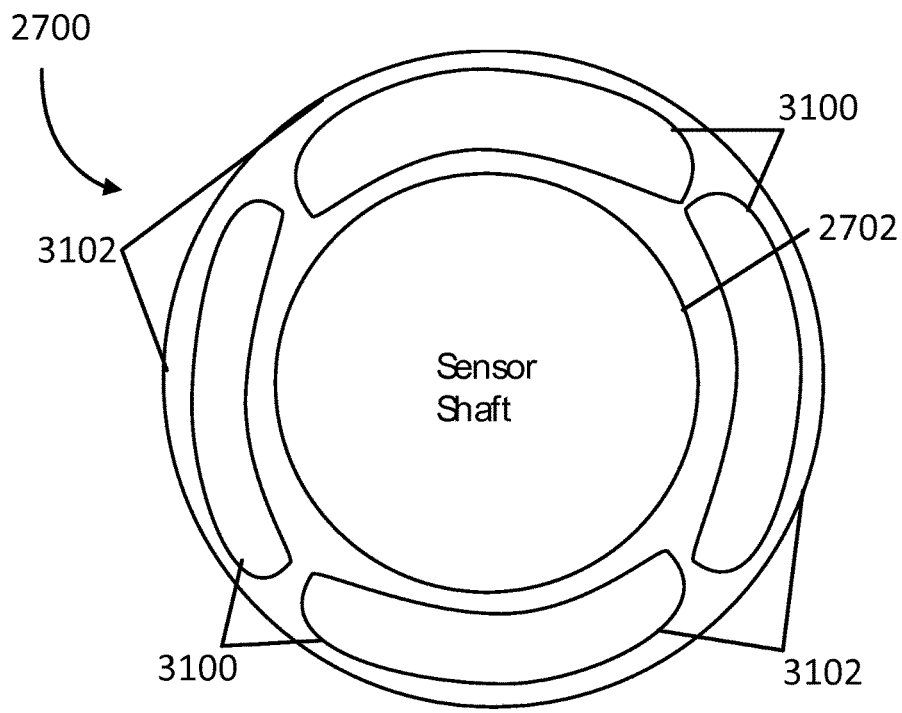
FIG. 33 illustrates a cross-sectional top view of another example device in accordance with embodiments of the present disclosure. The device shown in FIG. 33 does not include the pathways present in the devices shown in FIGS. 31 and 32. The covering is shown in a first position with the cavities deflated.
Figure 34:
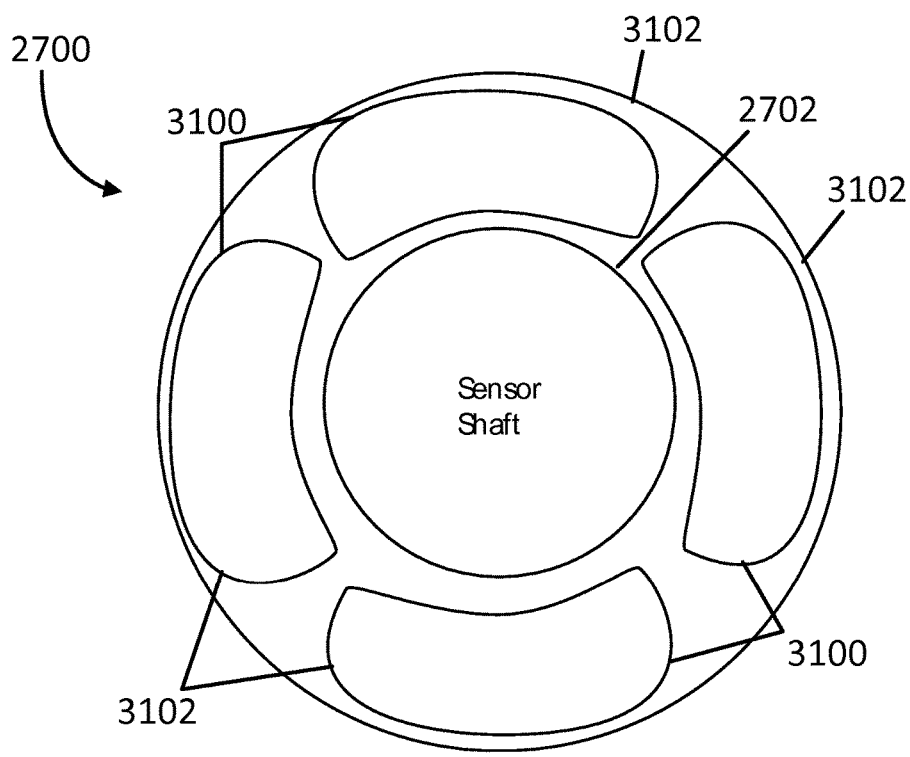
FIG. 34 illustrates a cross-sectional top view of the device shown in FIG. 33 except that the covering is shown in a position with the cavities inflated.

FIGS. 33 and 34 illustrate cross-sectional top views of another example device 2700 in accordance with embodiments of the present disclosure. The device 2700 shown in FIGS. 33 and 34 is similar to the device 2700 shown in FIGS. 31 and 32 except that the device 2700 shown in FIGS. 33 and 34 does not include the pathways 3104 shown in FIGS. 31 and 32. FIGS. 33 and 34 show the covering in a first position with the cavities 3100 deflated and inflated, respectively.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

EXAMPLES

Example 1: Experimental Set Up

FIG. 1 shows a schematic of the multilayer film structure according to an embodiment of the present disclosure as well as the procedure for the experiments performed in this section. Briefly, biofilms were allowed to form on the sample surfaces (step 1). One batch of samples was actuated by applying an oscillating voltage while the other (control) was not (Step 2). Both the actuated and control samples were rinsed and stained with SYTO 13 (Steps 3 and 4). The bacteria density was then counted under a fluorescent microscope (Step 5).

Figure 2:
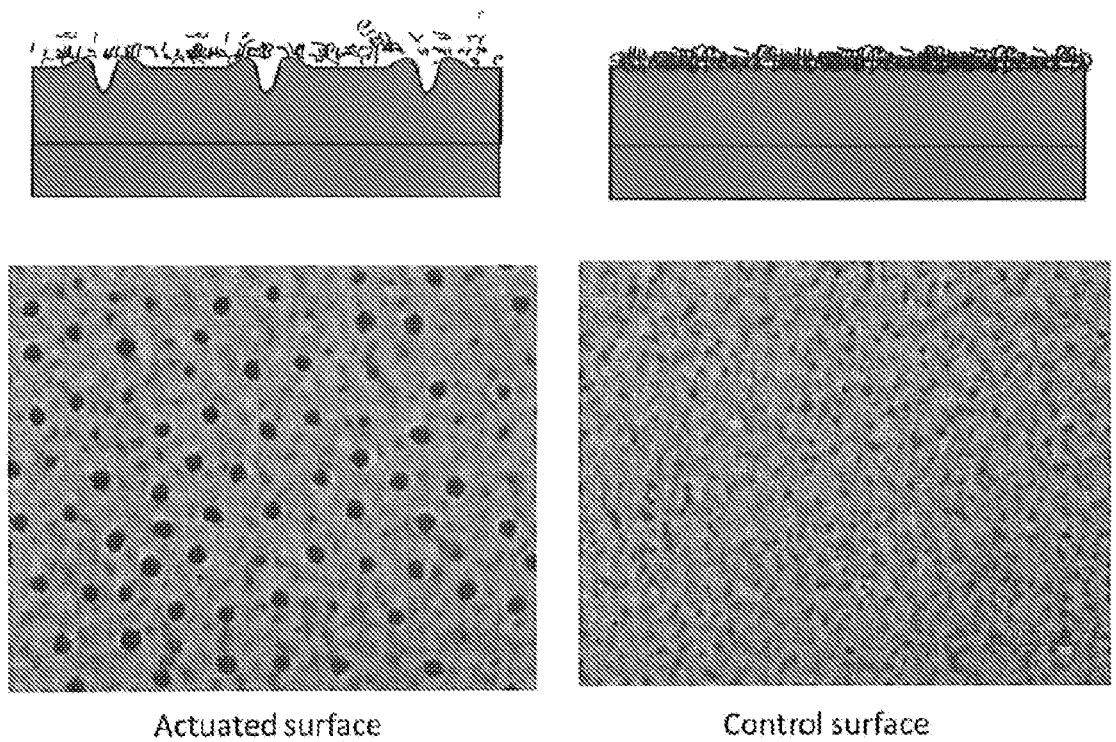
FIG. 2 are schematic side views and images showing that the biofilm on the actuated sample surface was detached due to the deformation of the polymer film, while the biofilm on the control sample surface was maintained.

Deformation of the polymer surface resulted in the detachment of the biofilm. As shown in FIG. 2, biofilms on the actuated sample surface (FIG. 2A) were detached due to the deformation of the polymer film, while the biofilm on the control sample surface was still maintained (FIG. 2B).

Figure 3:
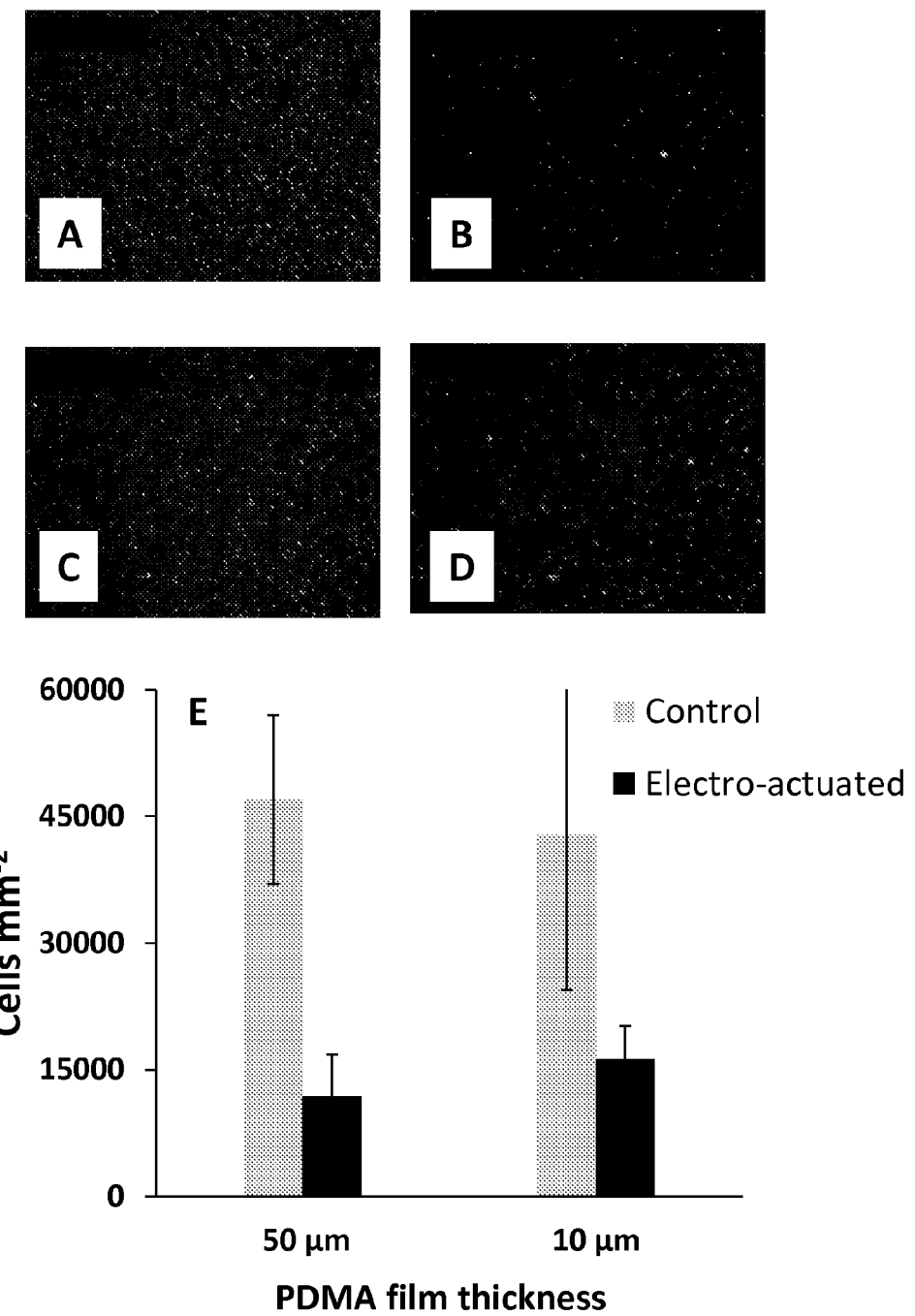
FIG. 3 are fluorescent microscope images showing C. marina cells on (A) control polymer film (50 µm thickness); (B) actuated polymer film (50 µm thickness); (C) actuated polymer film (10 µm thickness); and (D) control polymer film (10 µm thickness).

This detachment was further shown in FIG. 3 by fluorescent microscopy. Fluorescent microscope images showing C. marina cells on control (FIG. 3A) and actuated (FIG. 3B) polymer files of 50 mm, and control (FIG. 3C) and actuated (FIG. 3D) polymer films of 10 mm.

Figure 4:
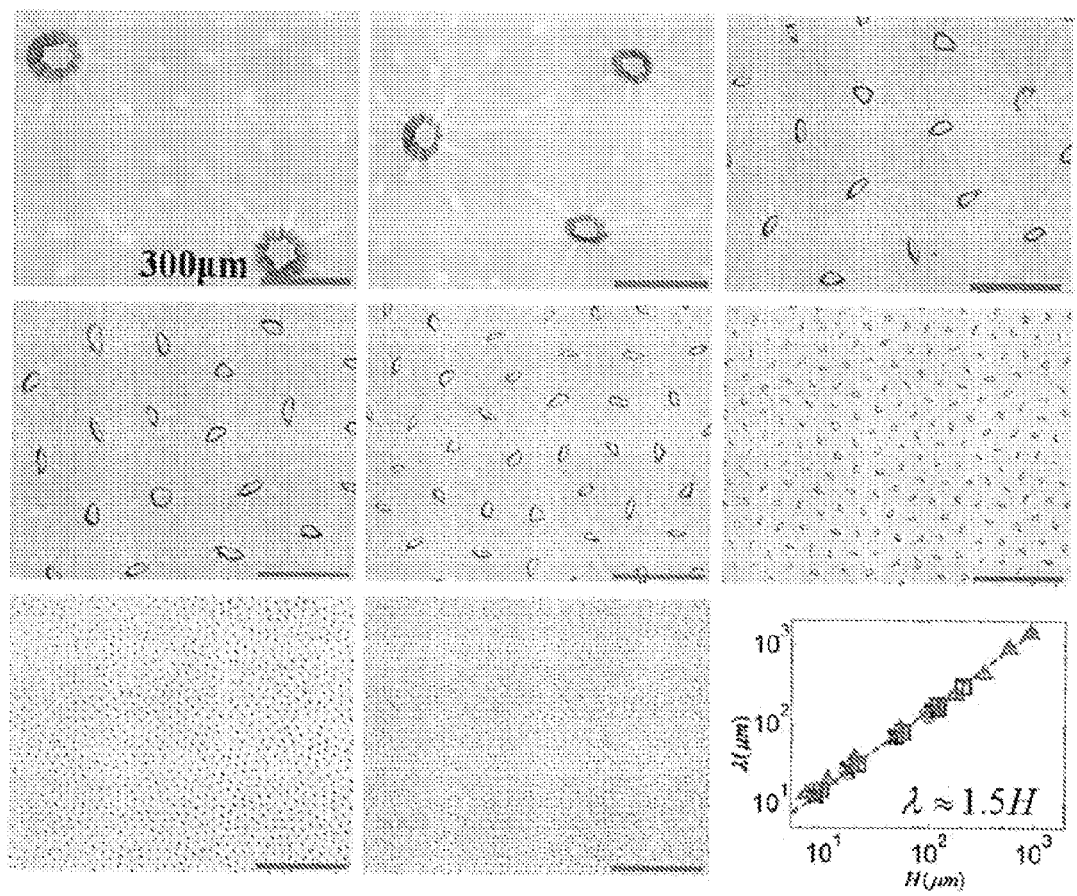
FIG. 4 is a graph a fluorescent microscope images demonstrating that the wavelength of the patterns generated on the soft polymer can be tuned from 1 mm to 1 µm by varying the thickness of the soft polymer. The wavelength (λ) is 1.5 times of the thickness of the polymer film.

As shown in FIG. 4, the wavelength of the patterns generated on the soft polymer can be finetuned from 1 mm to 1 μm by varying the thickness of the soft polymer. The wavelength is 1.5 times of the thickness of the polymer film.

Example II: Use of Electrical Actuation to Detach Bacterial Biofilms

Figure 5:
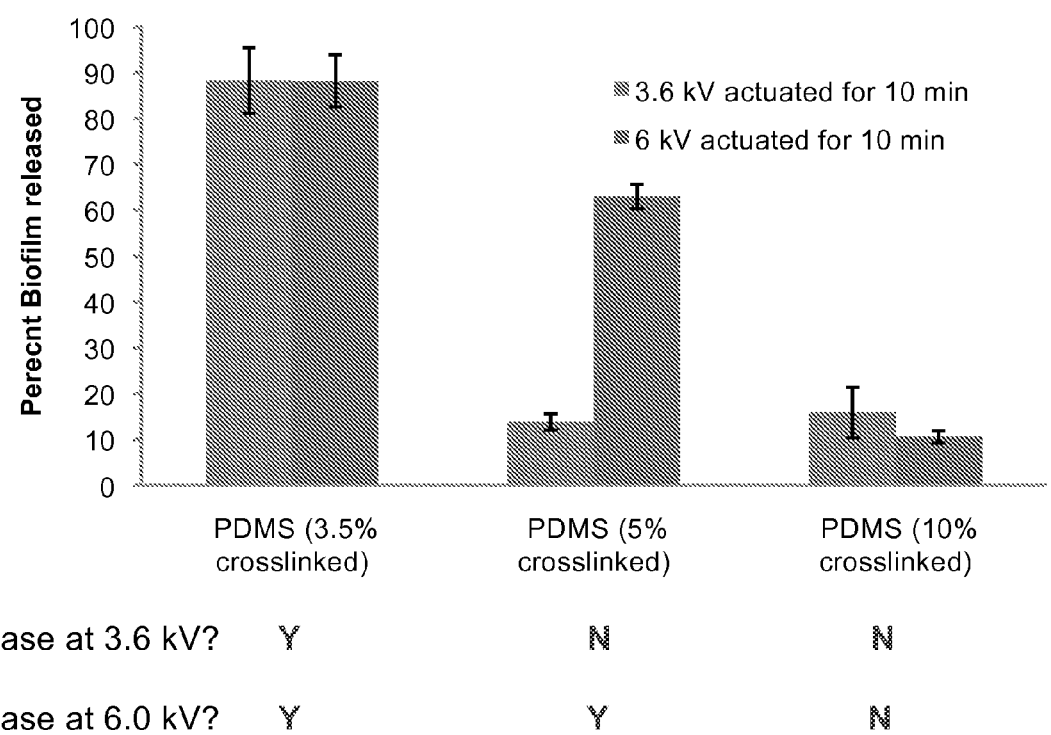
FIG. 5 is a graph showing the effect of electrical actuation on release of bacterial (C. marina) biofilms as measured by change in their fluorescence relative to control samples. Biofilms were formed on the surface of different elastomer films for 4 days. Electrical actuation was achieved by cycling the voltage between 0 V and 20 V for 20 min (0.2 Hz) while the media above the surface was constantly displaced (rinsed) at low shear using a continuous flow (0.5 mL/min).

Additional experiments were performed to provide evidence that release of biofilms is due to deformation of the elastomer film surface under actuation. FIG. 5 presents data in which biofilm release from surfaces of elastomer films (PDMS, SYLGARD 184, DOW CORNING INC.) of constant thickness, but different elastic modulus (varied by changing content of crosslinking agent from 3.5% to 10% by weight) was examined under two applied voltages, each oscillating to different amplitudes. The elastomer films are bonded on rigid polymer substrates (KAPTON, ~125 μm, DuPont). The voltages were chosen such that they each resulted in surface actuation (formation of dynamic surface corrugation, creases or "craters") for the lowest modulus sample, but not for the highest modulus sample. As indicated in FIG. 5, high levels of bacterial biofilm release were observed for films with low modulus at both actuation voltages, whereas low levels of release were observed for films with the highest modulus (10% crosslinker) at both actuation voltages. For the films with intermediate modulus (5% crosslinker) surface creasing was observed only for the higher level of applied voltage; the lower voltage was not sufficient to cause surface creasing of this film. Correspondingly, high levels of bacterial release were observed when the high alternative voltage was applied (6 kV) but not the lower voltage. These results provide evidence that the mechanism of biofilm release is due to the deformation of the polymer surfaces and is not due to the application of the electric field per se.

Figure 6:
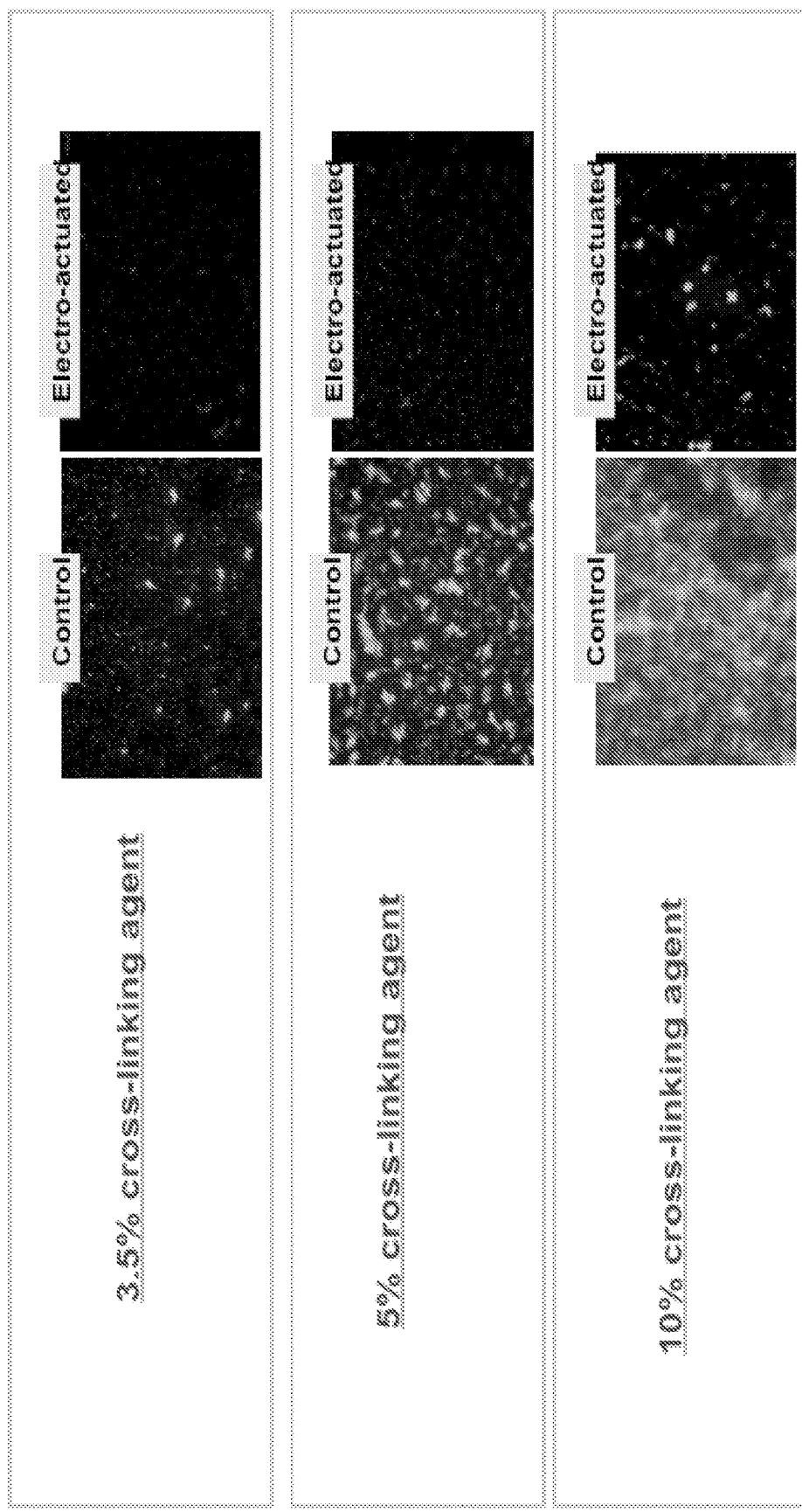
FIG. 6 are images showing the effect of modulus of PDMS dielectric elastomer films on release of C. marina biofilms with constant crease size. Biofilms were formed by exposing surfaces to bacterial suspension for 4 days. Electrical actuation was achieved by imparting an oscillating voltage sufficient to form creases of approximately the same size on all samples (20~μm) for 20 min while the solution above the surface was constantly displaced (rinsed) at low shear using a continuous flow (0.5 mL/min).

FIG. 6 presents microscopic data that indicates that dynamic surface corrugation can be used to affect biofilm release on elastomer films that have different modulus and differing amounts of attached biofilm. For elastomer films that varied in the modulus (containing varying amounts of crosslinking agent from 3.5% to 10% by weight), exposure to bacterial suspensions for 4 days resulted in the formation of biofilms with different character (see FIG. 6). A greater degree of biofouling was observed on films with higher modulus (higher crosslinker concentration). To examine the release of these biofilms on these different substrates, a time varying voltage was applied to each. The amplitude of the voltage was adjusted to achieve approximately the same maximum crease size (~20 μm). These data indicate that this level of surface corrugation was sufficient to result in a substantial amount of biofilm in each case.

While the data in FIGS. 5 and 6 clearly indicate that application of oscillating voltage to elastomer films with different modulus can be used to remove biofilms from their surface, and that the mechanism of biofilm is related to the formation of surface corrugation, the mechanism by which surface corrugation results in biofilm release remains to be elucidated.

Figure 7:
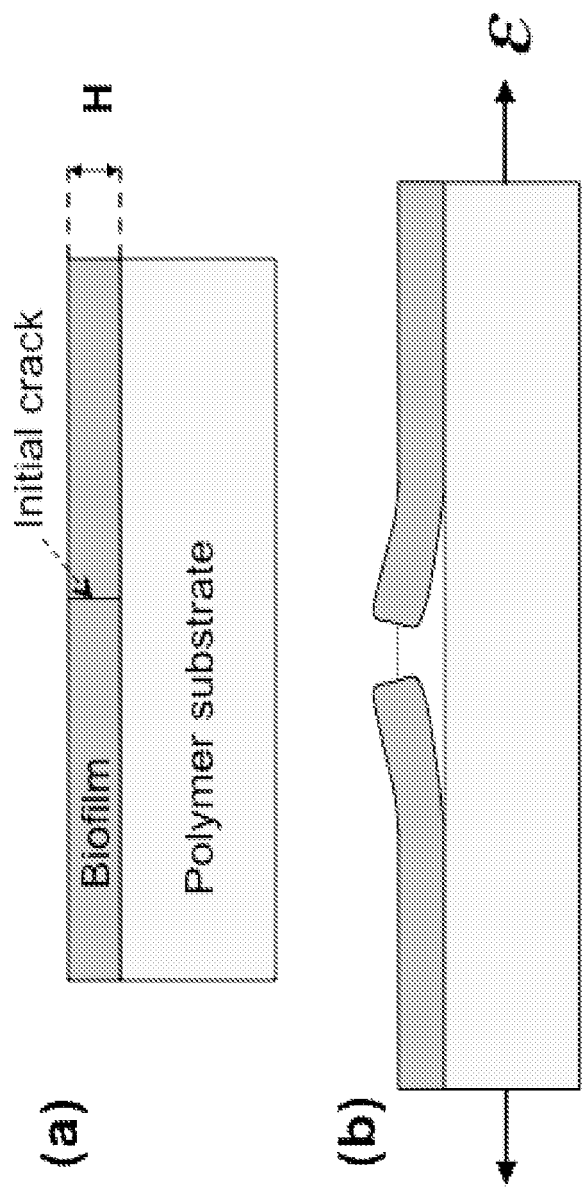
FIG. 7 provides a schematic representation of a likely mechanism for release of biofilms from elastomeric surfaces that experience surface deformation, or more precisely, a change in surface area due to externally applied strain, s, on the polymer substrate.

Example III: Postulated Mechanism for Active Control of Biofouling and Biofilm Release Via Active Surface Deformation FIG. 7 provides a schematic representation of a likely mechanism for release of biofilms from elastomeric surfaces that experience surface deformation, or more precisely, a change in surface area due to externally applied strain, ε, on the polymer substrate.

The interfacial energy between the biofilm and substrate per unit area is Γ. The elastic energy released in the biofilm per unit area of debonded region is W(ε)H, where W is the elastic energy density of the biofilm, and H the thickness of the biofilm.

Debonding of the biofilm occurs at a critical strain $\varepsilon_c$, when:

$$\Gamma = W(\varepsilon_c)H$$

If the biofilm behaves as a linear elastic material, the critical strain for debonding is:

$$\varepsilon_C = \sqrt{\frac{2\Gamma}{EH}}$$

where E is the Young's modulus of the biofilm.

This equation predicts that the critical strain necessary for debonding, and that which is necessary for release of the biofilm, is inversely proportional to the square root of the biofilm thickness.

Thus a simple means to examine the veracity of this mechanism of debonding and biofilm release is to vary the thickness of the biofilm and examine the extent of strain necessary to achieve its release. The above analysis indicates that thicker biofilms can be released at smaller fractional changes in surface area, a result that might seem to be counter-intuitive, but that will also have significant implications for design of active systems for control of biofouling.

Figure 8:
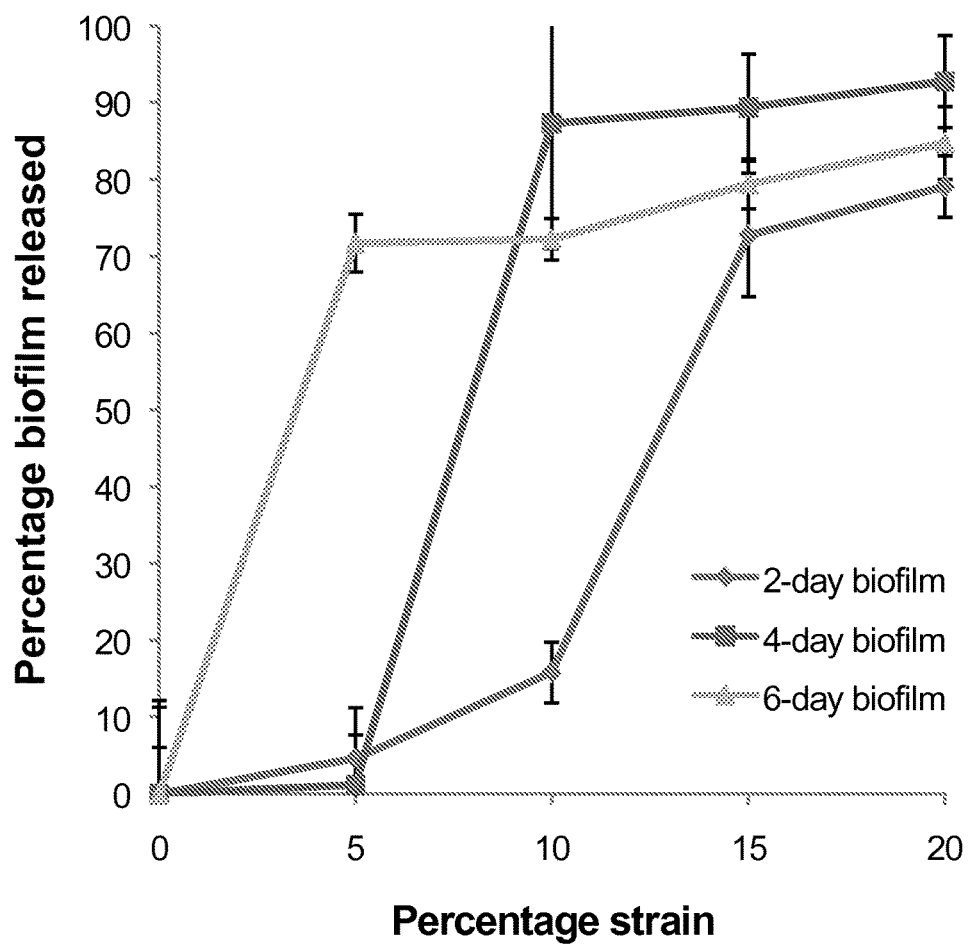
FIG. 8 is a graph showing biofilm retention vs. fractional extension in surface area.

Example IV: Extension of Interfacial Area Leads to Adhesive Failure of Biofilms and Enables Biofilm Release Biofilms of *C. marina* were formed on surfaces of an elastomer (ECOFLEX SUPERSOFT 0010, SMOOTH-ON, INC.) by exposing the elastomer surface to bacterial suspensions for times ranging from 2 days to 6 days. Visually it was apparent that as the biofilms that were formed for longer periods of time, they became thicker. After the specified biofilm formation time, the elastomer films with their associated biofilms were subjected to repeated strain. During stretching cycles, the media above the biofilm surface was under a constant flow (sterilized artificial sea water at a rate of 0.5 mL/min). The flow conditions were such that a low shear was applied to remove the detached or loosely adhering biofilm. Each sample was subjected to defined strain and release for 25 cycles with an approximate cycle time of 7.5 sec/cycle. FIG. 8 shows the amount of biofilm released, as estimated by decrease in fluorescence intensity for the biofilms of different thickness that were subjected to varying fractional extension in area. These data conform to the hypothesis that thicker biofilms exhibit a smaller critical strain for debonding ($\varepsilon_c$) and can thus be released from elastomer surfaces at smaller fractional extensions.

This important result strongly suggests that extension of the interfacial area between an attached biofilm and an elastic surface beyond the critical strain for debonding ($\varepsilon_c$) is a general means by which to release adherent biofilms and biofouling. There are many possible ways to achieve such extension in interfacial area, of which electrical actuation as described in the present disclosure is just one. In cases in which it is not possible or feasible to impose electrical voltage on elastic surface for biofilm release, other means for increasing interfacial area beyond $\varepsilon_c$ may be desirable. Such means can include: (a) stretching of an elastomer surface; (b) wrinkling an elastomer surface by imposition of a differential pressure across its surface; and (c) extension of the radius in tubular or spherical elastomer geometries.

Such mechanisms can find application in debonding of a number of biological films and adsorbates including those formed by: (i) marine and industrial biofouling; (ii) culture of mammalian cells; (iii) formation of infectious biofilms on medical implants.

An example of the latter is the problematic infectious biofilms that can form on medical implants such as indwelling catheters, which are often constructed of elastomers. The above analysis demonstrates that problematic biofilms can be released from such catheters by subjecting their surfaces to cyclic changes in surface area.

Example V: Voltage-Induced Dynamic Topology of Polymer Surfaces can Actively and Effectively Detach Adherent Biofilms (FIG. 9a) illustrates the structure of an electro-active antifouling coating. A rigid polymer substrate, KAPTON, (DUPONT, USA) with Young's modulus of 2.5 GPa and thickness of 125 μm was sputter-coated with a 10 nm gold layer underneath. A 50 μm polydimethyl siloxane (SYLGARD 184 DOW CORNING, USA) film was spin coated on top of the KAPTON film and cured at 65° C. for 12 hours. The crosslinker density of the SYLGARD 184 was varied from 2% to 10% to obtain elastomer films with shear moduli ranging from 60 kPa to 365 kPa. The thickness and shear modulus of the film were measured by DEKTAK 150 Stylus Profiler (BRUKER AXS, USA) and a uniaxial tensile tester (TA INSTRUMENTS, USA), respectively.

Figure 9:
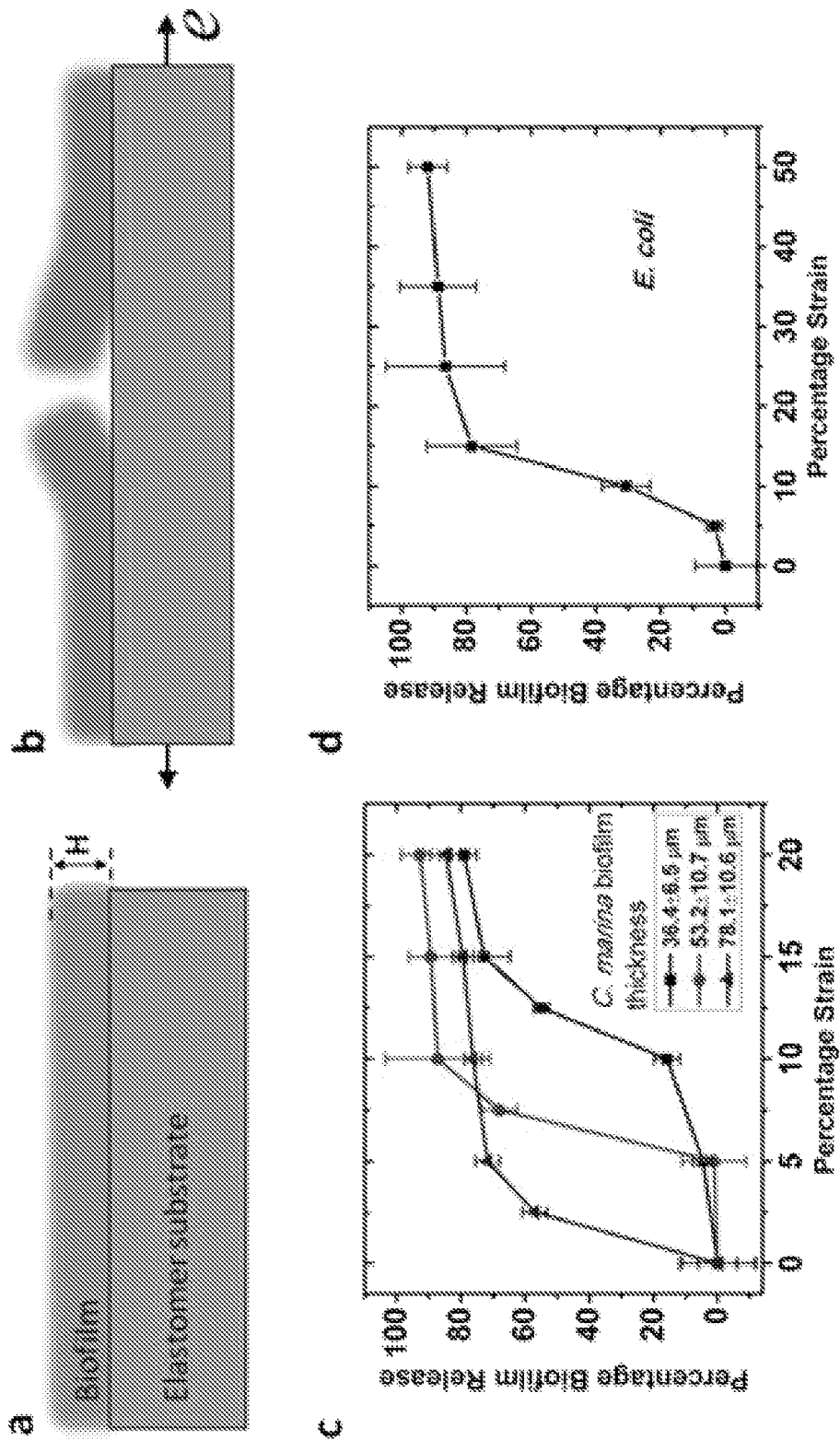
FIG. 9 illustrates detachment of bacterial biofilms from dielectric elastomers under voltages. (a) Schematic illustration of the laminate structure, actuation mechanism and the detachment of a bacterial biofilm. (b) The applied electric field can induce significant deformation of the elastomer surface as given by the contours of maximum principal strain. (c) The deformation detaches over 95% of a biofilm (C. marina) adhered to the elastomer surface, which is periodically actuated for 200 cycles within 10 minutes. (d) Illustrates a graph showing percentage biofilm release and percentage strain (E. coli).

Films of a silicone elastomer, a rigid insulating substrate, and a metal foil were bonded together to form a trilayer laminate. (Wang et al., 2011). The laminate can be readily fabricated to cover large areas. The elastomer surfaces were exposed to artificial-seawater suspensions of a model marine bacterium, Cobetia marina ($7 \times 10^7$ cells/mL), which is known to colonize many materials rapidly and to mediate the attachment of other fouling organisms in seawater (Maki, et al., 1995), and allowed to form biofilms for 4 days (FIG. 9a). The elastomer surfaces were electrically grounded by placing a ground electrode into artificial seawater, which flowed gently over the surface of the attached biofilm. Control studies showed that the flow alone does not detach biofilms (data not shown). Analysis of the biofilm detachment on control and electroactuated samples was performed by staining the biofilm using SYTO 13 (INVITROGEN INC.); the procedure is detailed elsewhere (D'Souza et al., 2010). The stain-washed biofilm surface was air dried in the dark for about 30 minutes and analyzed using a fluorescent microscope (ZIESS AXIO OBSERVER) using a 10× objective. At least five images at different regions were captured from each stained surface under same exposure time. The average percentage of biofilm detached from the surfaces was calculated by comparing the relative fluorescence intensities between the experimental and control samples. As a DC voltage was applied to the metal foil under the laminate, an electric field developed in the elastomer. When the electric field exceeds a critical value, the surface of the elastomer became unstable, deforming into a pattern of "micro-craters" (FIGS. 9a and 9b).

The critical electric field for the cratering instability can be expressed as (Wang et al., 2011)

$$E_c \approx 1.5\sqrt{\mu/\varepsilon} \qquad (1)$$

where $\mu$ and $\varepsilon$ are the shear modulus and dielectric constant of the elastomer. When the electric field was removed, the elastomer returned to its initial, flat topography. The surface strain of the elastomer was characterized under electric fields by imprinting markers on its surface (FIG. 9b). The size of the markers is much smaller than that of the craters and the markers form a regular square lattice on the undeformed surface. The surface strain is calculated by tracking the relative displacements of the markers (data not shown). In brief, the markers were fabricated by casting a 50 μm thick SYLGARD 184 film on a silicon mold with pillars arranged in a square lattice generated with photolithography. The distance between two adjacent pillars (5 μm) is much smaller than the thickness (50 μm) of the SYLGARD 184 film. Therefore, the markers have negligible effect on the deformation of the SYLGARD 184 film. Images (data not shown) of the SYLGARD 184 surface at flat and deformed states were captured through a microscope (Nikon, Japan). The initial ($X_j$) and deformed coordinates ($x_i$) were measured with an image processing software (IMAGEJ, NIH, USA) and the deformation gradient $$F_{iJ} = \frac{\partial x_i}{\partial x_J}$$

was computed using unite element analysis (T. J. R. Hughes, Dover Publications, 2000). The Green strain was then calculated as $E = (F^T F - I)/2$, where I denotes the Kronecker delta tensor. FIG. 9b gives the distribution of the maximum principal strain on the deformed surface. It can be seen that the maximum principal strain is over 20% on most area of the surface. After 200 on-off cycles of the applied voltage in 10 min, over 95% of the biofilm on the elastomer surface is detached (FIG. 9c). These data indicate that voltage-induced dynamic topology of polymer surfaces can actively and effectively detach adherent biofilms.

It was hypothesized that the deformation of the elastomer surface, and not the presence of the electric field, causes biofilm detachment. To test this hypothesis, the effects of the voltage and surface deformation on biofilm detachment were decoupled using a number of silicone elastomer layers with moduli ranging from 60 kPa to 365 kPa. Biofilms of C. marina were grown on the elastomer surfaces according to the following description. Cobetia marina (basonym, Halomonas marina) (ATTC 4741) and Escherichia coli (ATTC 15222) in marine broth (MB) (2216, Difco, ATTC, USA) and trypsin soy broth (TSB), respectively, containing 20% glycerol were stored frozen in stock aliquots at −80° C. Artificial seawater was prepared as reported previously (Ista et al., 1999). Experimental stock preparations were maintained on agar slants and were stored at 4° C. for up to 2 weeks. A single colony from an agar slant was inoculated into 50 mL of MB (for C. marina) or TSB (for E. coli) and grown overnight with shaking at 25° C. (C. marina) or 37° C. (E. coli). The bacterial concentrations were $7 \times 10^7$ cells mL$^{-1}$ and $11 \times 10^7$ cells mL$^{-1}$ for C. marina and E. coli, respectively. The surfaces used for growing biofilms were sterilized by rinsing several times with ethanol and then with copious amounts of sterilized DI water. About 1 mL of the C. marina or E. coli bacterial culture was placed on the sample surface along with 5 mL of sterilized artificial seawater or TSB broth. The samples were stored for a desired period in an incubator maintained at 26° C. for C. marina and 37° C. for E. coli. The samples were carefully monitored, and about 1 to 2 mL artificial seawater or TSB broth was added as needed every day to compensate for dehydration. The thicknesses of biofilms were measured by inverted confocal microscope (ZEISS LSM 510) (vide infra).

For the experiment to decouple voltage and surface deformation, the applied electric fields in the elastomers were controlled according to Eq. (1), such that the same electric field E can induce significant deformation for those elastomers where $E > E_c$ but not for those where $E < E_c$. A DC voltage was applied between artificial seawater and the bottom electrode by a controllable voltage supply (MAST-SUSADA, Japan). The voltage was switched on and off at a frequency of 0.33 Hz for 10 minutes on each sample with a continuous low-shear flow (0.5 mL/min) of artificial seawater to carry away the detached biofilms. The electric fields shown in Table 1 below were calculated using $$E = \Phi / \left(h + \frac{H_S \varepsilon}{\varepsilon_S}\right),$$

where $\Phi$ is the applied voltage, h is the thickness of SYLGARD 184 film, $H_s = 125$ μm is the thickness of the substrate, $\varepsilon = 2.65\varepsilon_o$ and $\varepsilon_s = 3.5\varepsilon_o$ are the dielectric constants of SYLGARD 184 and Kapton respectively, where $\varepsilon_o = 8.85 \times 10^{-12}$ Fm$^{-1}$ is the permittivity of vacuum. The percentage of C. marina biofilm detached (%) from SYLGARD 184 films with various moduli and under a range of applied electric fields is shown in Table 1. The crosslinker density of the SYLGARD 184 was varied to obtain elastomer films with shear moduli ranging from ~60 kPa to 365 kPa. The electric field was periodically varied between zero and a certain value (as shown in Table 1) for 200 cycles in 10 minutes. Imposition of electric fields below $E_c$ caused no surface deformation and had a minimal percentage (~15%) of biofilm detached (denoted by dark grey cells in Table 1). Imposition of electric fields below $E_c$ resulted in formation of 'micro-craters' such that the surface switched reversibly from a flat state to a catering state resulting in a high percentage (~95%) of biofilm detachment (denoted by white cells in Table 1). Significant detachment of biofilms (i.e., >85%) occurred only on those surfaces that underwent deformation (white cells in Table 1). Although they were subjected to the same electric fields, the undeformed surfaces exhibited minimal detachment (i.e., <15%) of biofilms. These results suggest that surface deformation is the dominant mechanism for detachment of biofilms from the elastomer surfaces actuated by electric fields.

Example VI: Effect of Surface Deformation on the Detachment of Various Forms of Biofouling by Stretching The effect of surface deformation on the detachment of various forms of biofouling by stretching elastomers was studied without imposition of electric fields. Biofilms of different thicknesses on the elastomers were formed from *C. marina* and *Escherichia coli* by varying their time in culture (Costerton et al., 1995). Thereafter, each elastomer with biofilm was stretched uniaxially to a prescribed strain for 30 cycles within 3 minutes, while artificial seawater was gently flushed across the surface of the elastomer to carry away detached biofilm. More specifically, films of the silicone elastomer, ECOFLEX 00-10 (SMOOTH-ON, USA) were used to detach biofilms by mechanical stretching. The thickness and shear modulus of the ECOFLEX films was 1 mm and 10.4 kPa, respectively. After biofilms adhered to a film, the two ends of the film were clamped and stretched and relaxed in a periodic manner. The film was stretched to prescribed strains and relaxed for 30 cycles in 3 minutes, during which a continuous low-shear flow (0.5 mL/min) of artificial seawater was used to carry away the debonded organisms. After stretching, the percentage of biofilm detachment was measured as a function of the applied strain. FIGS. 10c and 10d show that surface deformation induces significant detachment of *C. marina* and *E. coli* biofilms (i.e. >80%) when the applied strain exceeds critical values ranging from 2% to 14%. The critical value of the applied strain depends on the thickness of the biofilm (FIG. 10c). Interestingly, a thicker biofilm requires a lower critical strain for significant detachment.

The detachment of biofilms was interpreted as being a debonding process from the substrate (J. W. Hutchinson and Z. Suo, 1992). Prior to debonding, the mechanical strain in the polymer layer and the biofilm is the same. If the biofilm is considered to be linear elastic at the deformation rates used in the current study (Shaw et al., 2004), the elastic energy per unit area in the biofilm can be expressed as $HYe^2/2$, where e is the applied strain, Y is the plane-strain Young's modulus of the biofilm, and H the thickness of the biofilm. First it was determined that biofilm maintains integrity over a length scale much larger than its thickness. This was determined by growing biofilms of *C. marina* on rectangular ECOFLEX surfaces for six days and then staining the biofilm according to the methods described herein above. The stained biofilm gave a uniform coverage over most of the ECOFLEX surface (data not shown). The ECOFLEX substrate containing the stained biofilm was then clamped on two opposing edges and manually slowly stretched in uniaxial direction to 20% strain. The substrate was held in the stretched state and observed under the microscope to examine the effect of surface deformation on biofilm morphology. The biofilms on the deformed substrate maintained integrity over a length scale much larger than the thickness of the biofilms (i.e. 30 µm-80 µm) (data not shown). Therefore, the detachment of the biofilm can be analyzed as a debonding process of a film. Given that the biofilm maintains integrity over a length scale much larger than its thickness, debonding occurs when the elastic energy of the biofilm exceeds the adhesion energy between biofilm and the polymer. Therefore, the critical applied strain for the detachment of biofilm can be expressed as $$e_c = \sqrt{\frac{2\Gamma}{HY}} \qquad (2)$$

where $\Gamma$ is the biofilm-polymer adhesion energy per unit area. Eq (2) predicts that the critical strain is a monotonically decreasing function of the biofilm thickness. The prediction is consistent with the experimental results in FIG. 10c, where a thinner biofilm requires a higher critical strain for detachment.

Example VII: Effect of Surface Deformation on Macrofouling Organisms

To examine the effect of surface deformation on macrofouling organisms, adult barnacles (*Amphibalanus* (=*Balanus*)*amphitrite*) (Rittschof et al., 2008) were reattached to the surfaces of elastomers (see FIG. 11 for an illustration of the debonding mechanism). Reattachment of barnacles was performed using a previously published protocol (Rittschof et al., 2008). Briefly, barnacles (*Amphibalanus* (=*Balanus*) *amphitrite*) were reared to cyprids, settled on T2 (a gift from North Dakota State University) and cultured to a basal diameter of 0.5 cm in about 7 weeks. Barnacles were pushed off the T2 surface and immediately placed on the test surfaces in air and incubated in 100% humidity for 24 hours. Thereafter, the surfaces were submerged in running sea water and fed with brine shrimp daily for 2 weeks and tested. After the barnacles were firmly reattached, the elastomer layers were stretched to various prescribed strains periodically and then the shear forces for detaching the barnacles were determined (Rittschof et al., 2008). The shear force for barnacle detachment was plotted as a function of the applied strain on the elastomer layer (FIG. 11d). Deformation of the polymer significantly reduced the shear force required for detachment. For instance, an applied strain of 25% on the SYLGARD 184 substrate reduced the detachment force by 63%, and an applied strain of 100% fully detached the barnacles. The debonding process of a barnacle due to substrate deformation can be understood as the symmetric propagation of two cracks at the barnacle-polymer interface (FIG. 11b). The cracks will propagate if the decrease of the elastic energy of barnacle-polymer system exceeds the adhesion energy between barnacle and polymer substrate (Lu et al., 2007). The base plate of the barnacle is much more rigid than the polymer substrate (Ramsay et al., 2008). The substrate under a row of barnacles (FIG. 11c) is assumed to deform under a plane-strain condition (FIGS. 11a and 11b). The energy release rate due to crack propagation (i.e., the decrease of the system's elastic energy when the crack propagates a unit area) can be expressed as $G=\mu_s Lf(e,L/S)$, where $\mu_s$ is the shear modulus of the polymer substrate, L the length of the adhered region between barnacle and substrate, S the width of the substrate, and f a non-dimensional function calculated according to the following description by finite-element calculation. S4. Energy release rate for debonding of barnacles. The system of a row of barnacles on an elastomer film (FIG. 11c) was simplified as a 2D plane-strain model (data not shown). The ECOFLEX film was modeled as a Neo-Hookean material with shear modulus $\mu_s$ and was assumed to be infinitely thick. The barnacle was modeled as a rigid body. The bonding length between the barnacle and the polymer substrate is denoted as L. The energy release rate was computed by a commercial finite element package ABAQUS 6.10.1 (SIMULIA, USA) (data not shown). If the deformation is small (<10% strain), the energy release rate follows $$G = \mu_S Se^2 \tan\left(\frac{\pi L}{2S}\right) \tag{S1}$$

where S is the width of the polymer film (Lu et al., 2007). The energy release rate was determined to increase with the polymer shear modulus $\mu_s$ and the normalized contact length L/S (data not shown). The initial parts (i.e., low strain values) of the curves matched consistently with the theoretical result. From this experiment, G was shown to be a monotonically increasing function of $\mu_s$, e and L. Equating the energy release rate G with the adhesion energy between barnacle and substrate Γ, provides $$\Gamma = \mu_s Lf(e, L/S) \tag{3}$$

The adhesion length L between barnacle and substrate at any applied strain e can be calculated by solving Eq. (3). From FIG. 11d, it can be seen that the adhesion strengths for barnacle-SYLGARD 184 and barnacle-ECOFLEX systems are approximately the same. However, the SYLGARD 184 has a much higher shear modulus than the ECOFLEX, and so, when subjected to the same applied strain, the SYLGARD 184 substrate should detach barnacles more effectively (i.e. giving smaller L) than the ECOFLEX substrate. This prediction is consistent with the experimental results (FIG. 11d).

Figure 12:
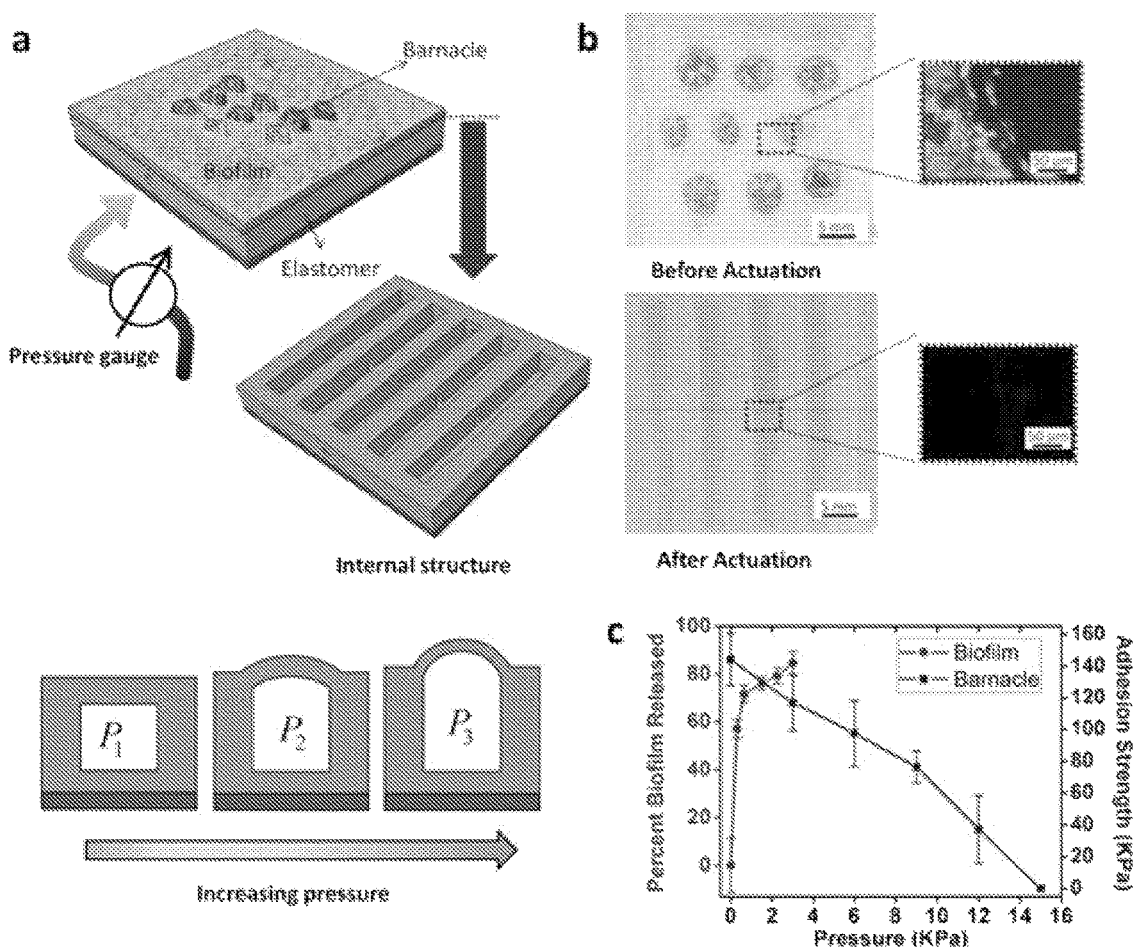
FIG. 12 illustrates detachment of bacterial biofilms from dynamic surfaces actuated by pressurized air. (a) Schematic of the structure of the dynamic surface colonized by both a biofilm of C. marina and barnacles, (b) photos and fluorescent microscope images of the surface before and after actuation, and (c) the percentage of biofilm detachment and the detachment shear stress for barnacles as functions of applied pressure. The dynamic surfaces are actuated for 30 cycles within 3 minutes.
Figure 13:
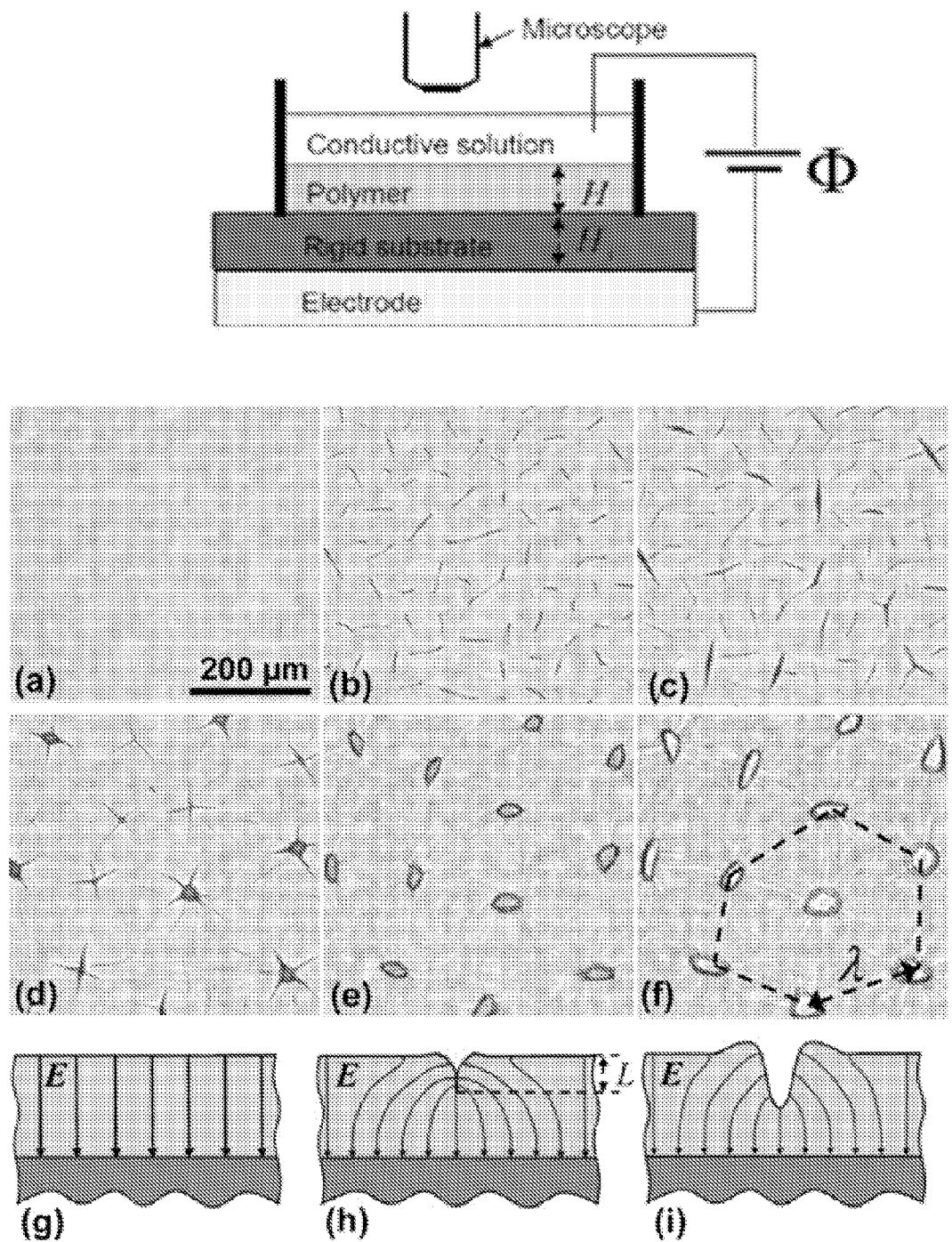
FIG. 13 illustrates the instability of elastomer coatings under high electric-field. The driving force for the instability is the electric-field-induced stress in the film. Panels (a)-(f) are images of the elastomer coatings after application of the electric field. Panels (g)-(i) show the direction of the applied electric field.
Figure 14:
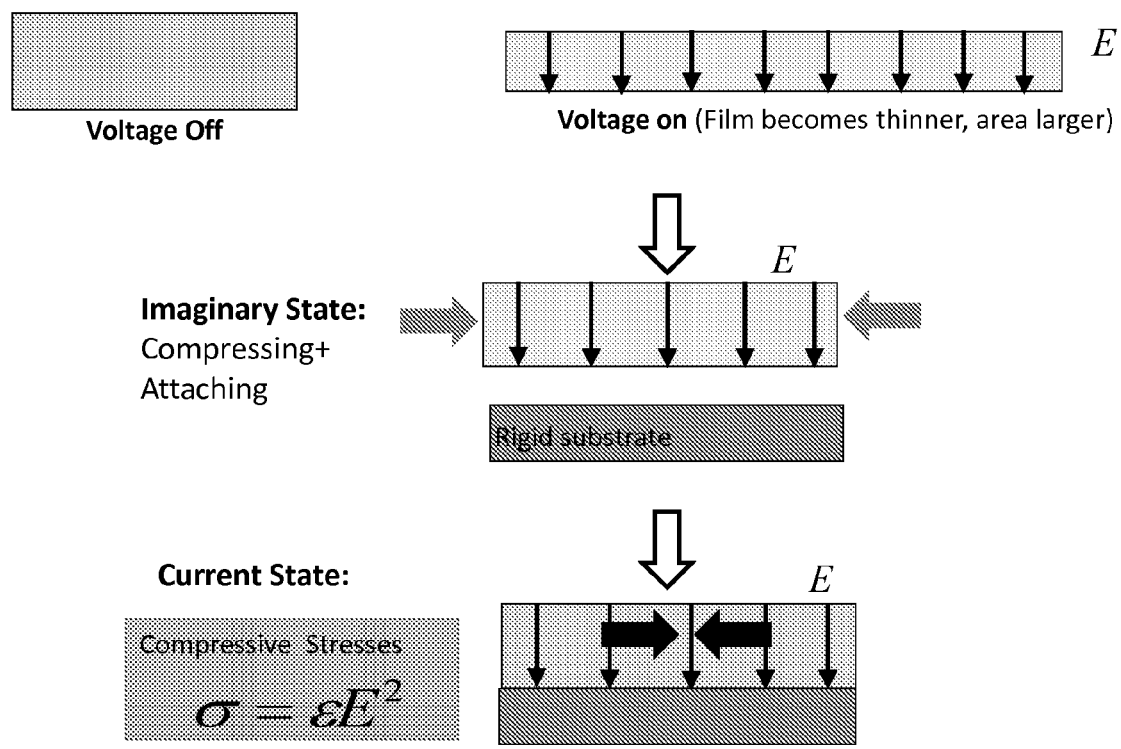
FIG. 14 illustrates the application of an electric-field to induce a change of shape in films on a rigid substrate.
Figure 15:
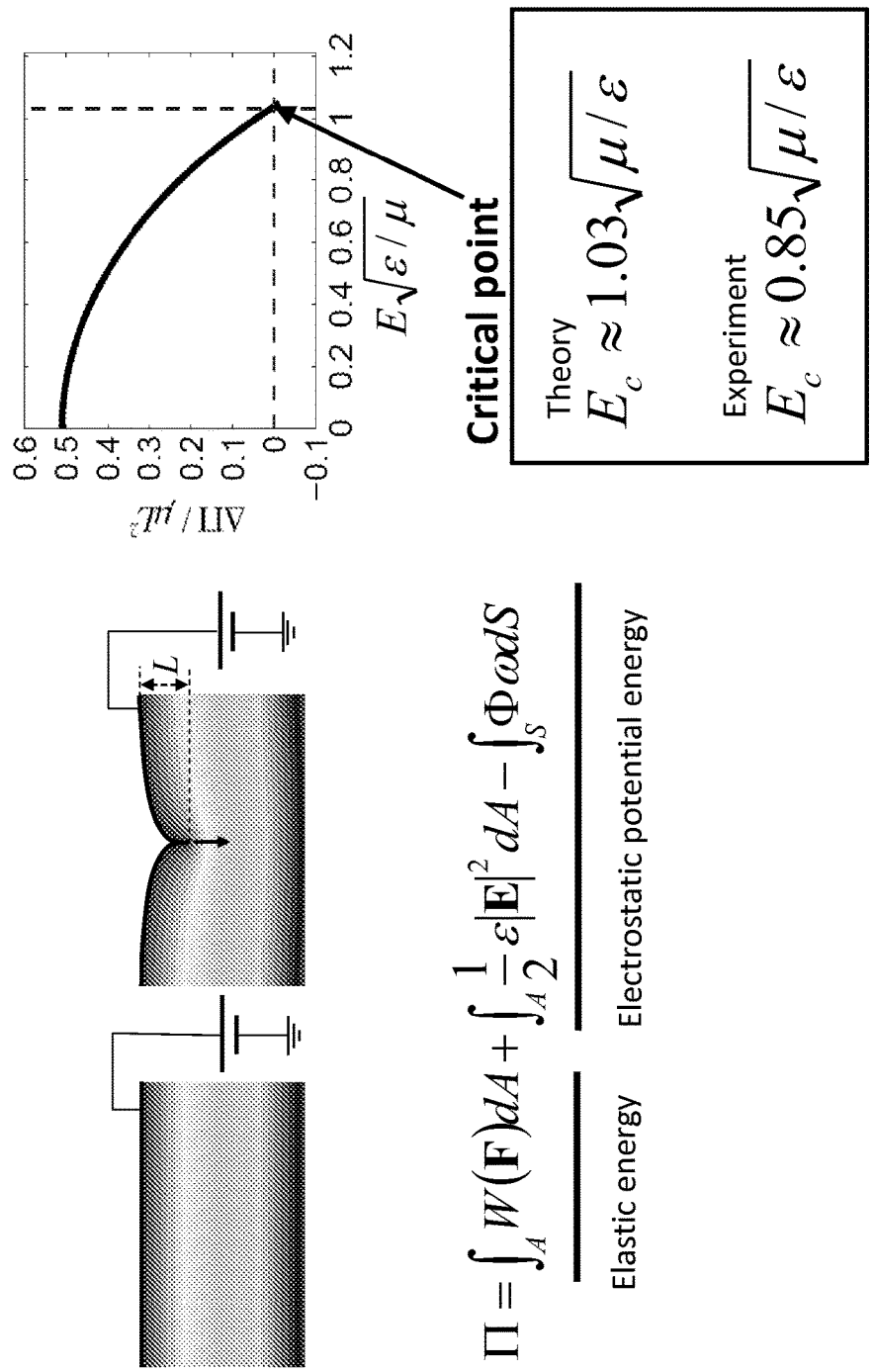
FIG. 15 illustrates the relationship between the theory and the experimental results for the critical point for inducing a change in shape for an elastomer film.
Figure 16:
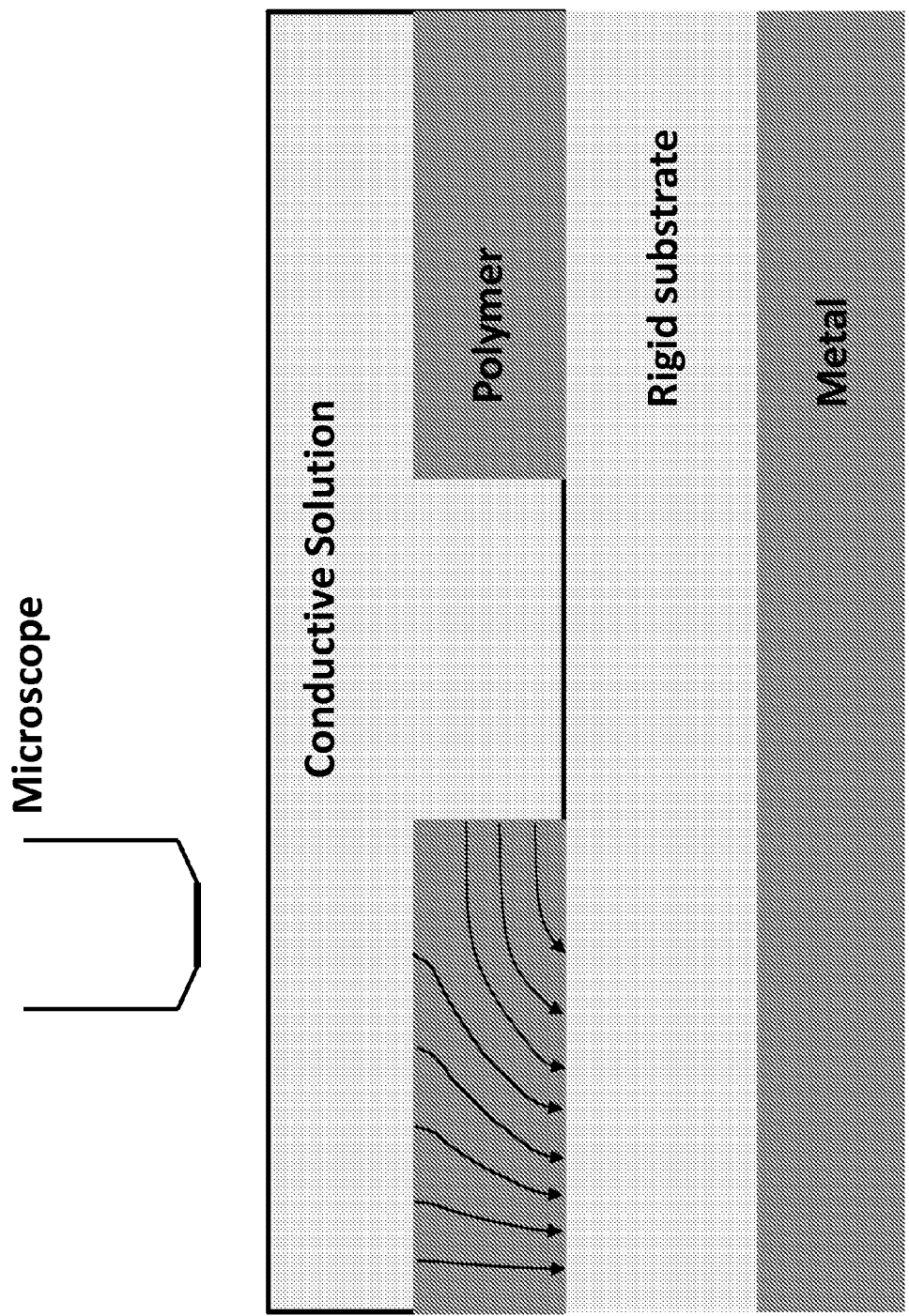
FIG. 16 is side view of a device for in accordance with embodiments of the present disclosure.

Example VIII: Pneumatic Networks for Active Detachment of Micro- and Macro-Biofouling Models As an alternative means for achieving surface deformation, the use of pneumatic networks (Ilievski et al., 2011) was examined for active detachment of micro- and macro-biofouling models. Biofilms of C. marina were grown on the surface of elastomers for 7 days after adult barnacles were reattached to the surfaces and grown as described herein above. As illustrated in FIG. 12a, air channels were fabricated beneath the elastomer layer, while the bottom surface of the network was bonded to a rigid plate. The process for fabrication of the pressure-actuation prototype was to fabricate a plastic prototype using a 3D printer (STRATASYS, USA) as a mold to cast a patterned ECOFLEX layer with patterned air-pass channels inside. The ECOFLEX layer was then adhered to an uncured ECOFLEX film (~200 μm) spin-coated on a glass plate to bond the patterned ECOFLEX layer with the glass plate. After curing, the patterned ECOFLEX network was firmly bonded to the glass slide to form enclosed air channels. Each air channel was covered by a long ECOFLEX strip with thickness of ~1 mm. Small holes were punched on two opposite walls of the network: one connected to a rubber tubing for air inlet and the other to a digital pressure transducer (TACHIKARA, INC.). The ECOFLEX layers were then actuated using a pneumatic pump (MASTERFLEX). The pressure in the air channels was gradually increased, and the coverage of biofilms and detachment shear stress for barnacles were measured. By controlling the air pressure in the channels of the ECOFLEX layers, the surfaces of the layer was reversibly deformed for 30 cycles in 3 minutes. When air was pumped into the channels, the thin ECOFLEX strip above the air channel buckled upward and induced controlled surface deformation (see FIG. 12). As shown in FIG. 12, the dynamic elastomer surface of the pneumatic network can actively and effectively detach both biofilms and barnacles. For example, an air pressure of 3 kPa induced 23% surface strain and almost 100% detachment of the biofilm. To fully detach the barnacles, a higher pressure (~15 kPa) was required.

The relation between the air pressure and the strain of the surface was determined according to the following procedure. The pressure-controlled buckling of the ECOFLEX strip above the air channel network was modeled by constructing a 2D plane-strain model to account for the deformation of the long ECOFLEX strip (data not shown). The ECOFLEX strip clamped at two ends was subjected to a uniform pressure P, buckling out as an arc with radius R. The initial and blistered length was denoted as 2L and 2l, respectively, and initial and blistered thickness of the film as H and h. Force balance gives $$PR = \sigma_\theta h \tag{S2}$$

where $\sigma_\theta$ is the membrane stress. The two principal stretches in the film are $$\lambda_\theta = \frac{l}{L} = \frac{\theta}{\sin\theta}, \tag{S3}$$
$$\lambda_r = \frac{h}{H} = \frac{1}{\lambda_\theta}$$

where 2θ is the angle of the arc. The Ecoflex film obeys the Neo-Hookean model, i.e.

$$\sigma_\theta = \mu\lambda_\theta^2 - p_o, \sigma_r = \mu\lambda_r^2 - p_o \tag{S4}$$

where $p_o$ is the hydrostatic pressure in the elastomer. Given that the radial stress $\sigma_r \approx 0$, Eq. (S4) gives $$\sigma_\theta = \mu(\lambda_\theta^2 - \lambda_r^2) \tag{S5}$$

Combining Eqs. (S2, S3, S5), the relation was calculated between the applied pressure P and the surface strain of the ECOFLEX film $e = \lambda_\theta - 1$. The theoretical results consistently matched with the experimental data (data not shown). The data provided herein demonstrate antifouling capabilities of dynamic surfaces actuated by pneumatic networks. Hydraulic networks for deformation of elastomers (Thorsen et al., 2002) are expected to perform similarly.

Example VIV: Active Surface Distortion by Stretching to Facilitate Release of Encrustation by Viscoelastic and Crystalline Biofilms An in vitro bladder model was constructed to test for the ability to release encrustation by viscoelastic and crystalline biofilms in urinary catheter devices. The model consisted of a drip flow reactor maintained at 37° C. by mini-incubator. The media used for p. mirabilis was an artificial urine was composed of calcium chloride 0.49 g/L, magnesium chloride hexahydrate 0.65 g/L, sodium chloride 4.6 g/L, disodium sulfate 2.3 g/L, trisodium citrate dihydrate 0.65 g/L, disodium oxalate 0.02 g/L, potassium dihydrogen phosphate 2.8 g/L, potassium chloride 1.6 g/L, ammonium chloride 1.0 g/L, urea 25 g/L, and gelatin 5.0 g/L in deionized water. The pH of the medium was adjusted to 6.1 and then sterilized. TRYPTONE SOYA BROTH was prepared separately, autoclaved, and added to the sterile basal medium to a final concentration of 1.0 g/L; this made the total artificial urine media. The media for e. coli was NATURAL BROTH (NB) or TRYPTONE SOYA BROTH.

The in vitro bladder model consisted of a drip flow reactor maintained at 37° C. by mini-incubator. The drip flow reactor can have tubing, flat coupons, or catheter sections inside of it. The samples in the DFR were infected with either: 20 mL of a 4 h p. mirabilis bacterial culture in artificial urine, or 20 ml of a 24 hr e. coli culture in NB. The infected culture was left for 1 hour before the media supply was resumed.

Artificial urine media was continuously flowed through the model at a flow rate of 0.5 mL/min using a peristaltic pump. The model was run continuously until desired the time point, or a system blockage occurred. Samples were removed from the reactor and were stretched or surface distorted to desired amount, lightly rinsed, and then fluorescence stained. The fluorescence stain (CYTO 13) bonded to the extracellular matrix (ECM) as well as the cells. The fluorescence stained samples were then imaged and the fluorescence intensity was measured. The fluorescence intensity was used to calculate the percentage of biofilm release.

E. coli biofilm was grown on tubular samples (SILICONE TUBING, VWR) by exposing the elastomer luminal surface to bacterial suspensions and then supplying continuous flow of NB MEDIA for 7 days. Biofilm covered the exposed luminal surface. Control samples were not strain cycled but test samples were exposed to strains ranging from 10 to 50% for 20 cycles. 10% strain samples demonstrated 80% biofilm release and 50% strain samples demonstrated greater than 90% biofilm release. These results confirm that surface deformation effectively detached urinary biofilms with typical biofilm visco-elastic mechanical properties. Visual observation of fluorescence images confirmed that large portions of biofilm had been detached.

P. mirabilis biofilm was grown on flat coupon samples (DRAGON SKIN 0020, SMOOTH-ON, INC.) by exposing the elastomer surface to bacterial suspension and then supplying continuous flow of ARTIFICIAL URINE MEDIA for 1 day. Crystalline biofilm covered the exposed surface and crystalline structure was confirmed under microscope. Control samples were not strain cycled but test samples were exposed to strains ranging from 10 to 50% for 15 cycles. 10% strain samples demonstrated 50% biofilm release and 50% strain samples demonstrated greater than 90% biofilm release. These results confirm that surface deformation effectively detached crystalline urinary biofilms with higher modulus, and less visco-elastic, mechanical properties. Visual observation of fluorescence images confirmed the large portions of biofilm detached in deformed regions. Additionally, cracks were observed in remaining areas of biofilm in deformed regions.

P. mirabilis biofilm was grown on tubular samples (SILICONE TUBING, VWR) by exposing the elastomer luminal surface to bacterial suspension and then supplying continuous flow of artificial urine media for 2 days. Crystalline biofilm covered the exposed luminal surface and was visible with naked eye observation. Control samples were not strain cycled but test samples were exposed to strains ranging from 10 to 50% for 15 cycles. 10% strain samples demonstrated 68% biofilm release and 50% strain samples demonstrated greater than 98% biofilm release. These results confirm that surface deformation effectively detached crystalline urinary biofilms with higher modulus, and less visco-elastic, mechanical properties. The presumably thicker biofilm (due to 2 growth vs 1 day of growth) released to a larger percentage of biofilm at 10% strain and with less variability. This result supports the clinical application of the biofilm releasing technology; increased time between therapeutic biofilm detachment would be advantageous for the patient.

In summary, the deformation of polymer surfaces can effectively detach microbial biofilms and macro-fouling organisms. Inspired by active biological surfaces, simple elastomer surfaces were created capable of dynamic deformation in response to external stimuli including electrical voltage, mechanical stretching and air pressure. The use of dynamic surface deformation is complementary and can enhance other means for biofouling management such as surface modification, controlled release and micro- and nanotopography.

Any patents or publications mentioned in this specification are indicative of the levels of those skilled in the art to which the present disclosure pertains. These patents and publications are herein incorporated by reference to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present examples along with the methods, procedures, compositions, devices, systems, and apparatus described herein are presently representative of various embodiments, are exemplary, and are not intended as limitations to the scope of the presently disclosed subject matter. Changes therein and other uses well occur to those skilled in the art which are encompassed within the spirit of the presently disclosed subject matter as defined by the scope of the claims and outlined herein.

REFERENCES

1. Wang, Q. et al. (2011) Soft Matter, 7:6583.
2. Wang, Q. et al. (2011) Physical Review Letters 106: 118301.
3. Magin, C. M. (2010) Biofouling 26:719-727.
4. Cao, X. et al. (2010) Advanced Functional Materials 20: 1984-1993.
5. Q. Wang, M. Tahir, J. Zang, X. Zhao (2011) Advanced Materials 2012, DOI: 10.1002/adma.201200272; Q. M. Wang, L. Zhang, X. H. Zhao, Physical Review Letters, 106, 118301.
6. J. S. Maki, D. Rittschof, M.-Q. Samuelsson, U. Szewzyk, A. B. Yule, S. I (jelleberg, J. D. Costlow, R. Mitchell, BULLETIN OF MARINE SCIENCE 1990, 46, 499; C. R. C. Unabia, M. G. Hadfield, Marine Biology 1999, 133, 55; C. Shea, L. J. Lovelace, H. E. Smith-Somerville (1995) Journal of Industrial Microbiology, 15.
7. F. D'Souza, A. Bruin, R. Biersteker, G. Donnelly, J. Klijnstra, C. Rentrop, P. Willemsen (2010) J Ind Microbiol Biotechnol, 37, 363.
8. T. J. R. Hughes (2000) The finite element method: linear static and dynamic finite element analysis, Vol. 65, Dover Publications.

9. L. K. Ista, V. H. Pérez-Luna, G. P. López (1999) *Applied and Environmental Microbiology*, 64, 1603.
10. J. W. Costerton, Z. Lewandowski, D. E. Caldwell, D. R. Korber, H. M. Lappin-Scott (1995) *Annual Review of Microbiology*, 49, 711.
11. J. W. Hutchinson, Z. Suo (1992) *Advances in Applied Mechanics*, Vol 29, 29, 63.
12. T. Shaw, M. Winston, C. J. Rupp, I. Klapper, P. Stoodley (2004) *Physical Review Letters*, 93.
13. D. Rittschof, B. Orihuela, S. Stafslien, J. Daniels, D. Christianson, B. Chisholm, E. Holm (2008) *Biofouling*, 24, 1.
14. N. Lu, J. Yoon, Z. Suo (2007) *International Journal of Materials Research*, 98, 717.
15. D. B. Ramsay, G. H. Dickinson, B. Orihuela, D. Rittschof, K. J. Wahl (2008) *Biofouling*, 24, 109.
16. F. Ilievski, A. D. Mazzeo, R. E. Shepherd, X. Chen, G. M. Whitesides (2011) *Angewandte Chemie-International Edition*, 50, 1890.
17. T. Thorsen, S. J. Maerkl, S. R. Quake (2002) *Science*, 298, 580.

What is claimed:

1. A device comprising:
   a surface for contacting a biological material; and
   a mechanism comprising a structure configured to change the surface between a first shape and a second shape, wherein the change from the first shape to the second shape deforms the surface beyond a critical strain for debonding of a fouling agent from the surface when the fouling agent has bonded to the surface in the first shape,
   wherein the surface defines a lumen, and
   wherein the structure defines at least one cavity that substantially surrounds the lumen and configured to be inflated and deflated such that the cavity impinges on the lumen when inflated to change the surface from the first shape to the second shape and when deflated to change the surface back to the first shape.

2. The device of claim 1, wherein the surface defines a lumen.

3. The device of claim 1, wherein the surface defines a lumen of a catheter.

4. The device of claim 1, wherein the surface is defined by a material comprising a polymer.

5. The device of claim 1, wherein the surface is defined by a material comprising one of polydimethyl siloxane, silicone rubber, acrylic elastomer, polyurethane, or fluoroelastomer.

6. The device of claim 1, wherein the structure is configured to apply a mechanical force to the surface for changing the surface between the first shape and the second shape.

7. A device comprising:
   a surface for contacting a biological material; and
   a mechanism comprising a structure configured to change the surface between a first shape and a second shape, wherein the change from the first shape to the second shape deforms the surface beyond a critical strain for debonding of a fouling agent from the surface when the fouling agent has bonded to the surface in the first shape,
   wherein the surface is defined by a material, and
   wherein the structure is configured to apply pneumatic pressure to the material for causing the surface to change between the first shape and the second shape.

8. The device of claim 1, further comprising a high durometer sheath substantially surrounding the cavity.

9. The device of claim 1, wherein the lumen is a lumen of a catheter.

10. The device of claim 1, wherein the at least one cavity is fluidly connected to a pump port configured to inflate the at least one cavity.

11. The device of claim 10, wherein the pump port is configured to inflate the at least one cavity via application of pneumatic pressure.

12. The device of claim 1, wherein the lumen has a first side and a second side and wherein the first side and the second side come into contact in the second shape.

13. The device of claim 1, further comprising an aperture for a balloon structure configured to be inflated on an internal-positioned end and comprising an external-positioned inflation port configured for inflation of the internal-positioned end, such that inflation of the balloon structure after insertion holds the catheter in place.

14. The device of claim 1, wherein the catheter is a urinary catheter.

15. A device comprising:
    a surface for contacting a biological material; and
    a mechanism comprising a structure configured to change the surface between a first shape and a second shape, wherein the change from the first shape to the second shape deforms the surface beyond a critical strain for debonding of a fouling agent from the surface when the fouling agent has bonded to the surface in the first shape,
    wherein the surface defines a lumen,
    wherein the structure defines at least one cavity that substantially surrounds the lumen and impinges on the lumen in the first shape and configured to be deflated and inflated such that the cavity ceases to impinge on the lumen when deflated to change the surface from the first shape to the second shape.

16. The device of claim 1, wherein the surface defines a first lumen,
    wherein the device further comprises a second lumen fluidly connected to the first lumen at one or more positions along a length of the first lumen and configured to direct a flushing fluid into the first lumen.

* * * * *